United States Patent
Kainosho et al.

(10) Patent No.: US 9,739,732 B2
(45) Date of Patent: Aug. 22, 2017

(54) STABLE ISOTOPE-LABELED ALIPHATIC AMINO ACID AND NMR STRUCTURAL ANALYSIS OF PROTEIN USING SAME

(71) Applicant: TAIYO NIPPON SANSO CORPORATION, Tokyo (JP)

(72) Inventors: Masatsune Kainosho, Tokyo (JP); Tsutomu Terauchi, Tokyo (JP)

(73) Assignee: Taiyo Nippon Sanso Corporation, Tokyo (JP)

( * ) Notice: Subject to any disclaimer, the term of this patent is extended or adjusted under 35 U.S.C. 154(b) by 0 days.

(21) Appl. No.: 14/421,814

(22) PCT Filed: Feb. 18, 2013

(86) PCT No.: PCT/JP2013/053901
§ 371 (c)(1),
(2) Date: Feb. 13, 2015

(87) PCT Pub. No.: WO2014/027473
PCT Pub. Date: Feb. 20, 2014

(65) Prior Publication Data
US 2015/0212020 A1    Jul. 30, 2015

(30) Foreign Application Priority Data
Aug. 16, 2012 (JP) ................................ 2012-180615

(51) Int. Cl.
| | |
|---|---|
| *G01N 24/08* | (2006.01) |
| *C07D 207/16* | (2006.01) |
| *C07C 229/08* | (2006.01) |
| *C07C 229/24* | (2006.01) |
| *C07C 229/26* | (2006.01) |
| *C07C 229/36* | (2006.01) |
| *G01R 33/465* | (2006.01) |
| *C07K 1/13* | (2006.01) |
| *G01R 33/46* | (2006.01) |

(52) U.S. Cl.
CPC ......... *G01N 24/087* (2013.01); *C07C 229/08* (2013.01); *C07C 229/24* (2013.01); *C07C 229/26* (2013.01); *C07C 229/36* (2013.01); *C07D 207/16* (2013.01); *G01R 33/465* (2013.01); *C07B 2200/05* (2013.01); *C07K 1/13* (2013.01); *G01N 2333/91045* (2013.01); *G01N 2458/15* (2013.01); *G01R 33/4608* (2013.01); *G01R 33/4633* (2013.01)

(58) Field of Classification Search
None
See application file for complete search history.

(56) References Cited

U.S. PATENT DOCUMENTS

| | | |
|---|---|---|
| 7,608,248 B2 | 10/2009 | Kainosho et al. |
| 2005/0084452 A1 | 4/2005 | Kainosho et al. |
| 2009/0075388 A1 | 3/2009 | Kainosho et al. |

FOREIGN PATENT DOCUMENTS

| | | |
|---|---|---|
| WO | 03/053910 A1 | 7/2003 |
| WO | 2007/099934 A1 | 9/2007 |

OTHER PUBLICATIONS

"How to Prepare Samples for NMR", available at http://nmr.chem.umn.edu/samprep.html.*
Yuan et al., Journal of Labelled Compounds and Radiopharmaceuticals (1981) 18(4), 563-569).*
Miyanoiri Y., et al., Journal of Biomolecular NMR (2011), vol. 51, No. 4, pp. 425-435.
Kainosho M., et al., Nature (2006), vol. 440, pp. 52-57.
Takeuchi et al., J. Biomol. NMR, 2010, 47(1), p. 55-63.
Takeuchi et al., J. Am. Chem. Soc., 2008, 130(51), p. 17210-1.

* cited by examiner

*Primary Examiner* — Marcela M Cordero Garcia
*Assistant Examiner* — Catherine Mader
(74) *Attorney, Agent, or Firm* — Hoffmann & Baron, LLP

(57) ABSTRACT

Provided is a stable isotope-labeled aliphatic amino acid enabling the assignment of the signal of an amino acid residue side chain by increasing to the maximum the observation sensitivity to an NMR signal of the same amino acid residue side chain, and allowing NOE (nuclear Overhauser effect) between protons in the amino acid residue to be observed. The stable isotope-labeled aliphatic amino acid is for constituting a protein and satisfies all of the following conditions (1) to (3): (1) two or more carbon atoms are labeled with $^{13}C$; (2) of two or more carbon atoms labeled with $^{13}C$, a carbon atom other than a carbon atom of a methyl group, which is capable of bonding to a hydrogen atom, has one $^{1}H$ directly bonded thereto, while the carbon atom of the methyl group has at least one $^{1}H$ directly bonded thereto; and (3) other carbon atoms adjacent to all the $^{13}C$ are all $^{12}C$.

13 Claims, 16 Drawing Sheets

0.3 mM [Leu(2);$^2$H;$^{15}$N] MSG ( 200 ml M9 D$_2$O + 4mg L-12 )
20 mM Na Phosphate, 20 mM MgCl$_2$, 5 mM d10-DTT, 1mM NaN3, 0.01% DSS,
1% D$_2$O, pH 7.1, 310 K
aliphatic ctS3CT HSQC 2H dec @ 900 MHz CRYOPROBE, d1 = 1.5 sec Observed Leu β3 signals : ca. 66 / 70 residues 0.3 mM L-11-$^2$H$^{12}$C$^{15}$N MSG ( 200 ml M9 D$_2$O + 4mg L-11 )
20 mM Na Phosphate, 20 mM MgCl$_2$, 5 mM d10-DTT, 1mM NaN3, 0.01% DSS, 1% D$_2$O, pH 7.1, 310 K
aliphatic S3CT HSQC 2H dec @ 900 MHz CRYOPROBE, d1 = 1.5 sec 0.3 mM [L(2);$^2$H:$^{15}$N] MSG ( 200 ml M9 D$_2$O + 4mg L-12 )
20 mM Na Phosphate, 20 mM MgCl$_2$, 5 mM d10-DTT, 1mM NaN3, 0.01% DSS, 1% D$_2$O, pH 7.1, 310 K
aliphatic S3CT HSQC 2H dec @ 900 MHz CRYOPROBE, d1 = 1.5 sec

L180 : (χ1, χ2) = (-55.5° , -173.4°)

0.46 mM UL¹³C-Pro-²H¹²C¹⁵N MSG ( UL¹³C-Pro: 30mg/L)
20 mM Na Phosphate, 20 mM MgCl₂, 5 mM d10-DTT, 1mM NaN3, 0.01% DSS, 1% D₂O, pH 7.1, 310 K
aliphatic ct S3CT HSQC 2H dec @ 900 MHz CRYOPROBE, d1 = 4 sec

[UL-¹³C] Pro

31 Pro in MSG:
P26, P48, P72, P74, P93, P95
P115, P120, P149, P160, P179, P213
P226, P253, P347, P358, P391, P396
P417, P469, P480, P512, P536, P538,
P571, P580, P621, P675, P679, P704
P710

FIG.12 0.46 mM SAIL-Pro(Pro-1)-$^2$H$^{12}$C$^{15}$N MSG (SAIL-Pro: 30mg/L)
20 mM Na Phosphate, 20 mM MgCl$_2$, 5 mM d10-DTT, 1mM NaN3, 0.01% DSS, 1% D$_2$O, pH 7.1, 310 K
aliphatic ctS3CT HSQC 15N dec @ 900 MHz CRYOPROBE, d1 = 4 sec SAIL-Pro 31 Pro in MSG:
P26, P48, P72, P74, P93, P95
P115, P120, P149, P160, P179, P213
P226, P253, P347, P358, P391, P396
P417, P469, P480, P512, P536, P538,
P571, P580, P621, P675, P679, P704
P710

0.46 mM Pro-1-$^2$H$^{12}$C$^{15}$N MSG (SAIL-Pro: 30mg/L)
20 mM Na Phosphate, 20 mM MgCl$_2$, 5 mM d10-DTT, 1mM NaN3, 0.01% DSS, 1% D$_2$O, pH 7.1, 310 K
aliphatic ct S3CT HSQC 2H dec @ 900 MHz CRYOPROBE, d1 = 4 sec SAIL-Pro 31 Pro in MSG:
P26, P48, P72, P74, P93, P95
P115, P120, P149, P160, P179, P213
P226, P253, P347, P358, P391, P396
P417, P469, P480, P512, P536, P538,
P571, P580, P621, P675, P679, P704
P710

Observed Pro γ3 signals : 11 / 31 residues

FIG.15
0.46 mM Pro-$^2$H$^{12}$C$^{15}$N MSG ( Pro(3): 30mg/L)
20 mM Na Phosphate, 20 mM MgCl$_2$, 5 mM d10-DTT, 1mM NaN3, 0.01% DSS, 1% D$_2$O, pH 7.1, 310 K
aliphatic S3CT HSQC 2H dec @ 900 MHz CRYOPROBE, d1 = 4 sec
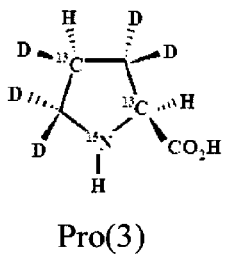
Pro(3)
31 Pro in MSG:
P26, P48, P72, P74, P93, P95
P115, P120, P149, P160, P179, P213
P226, P253, P347, P358, P391, P396
P417, P469, P480, P512, P536, P538,
P571, P580, P621, P675, P679, P704
P710
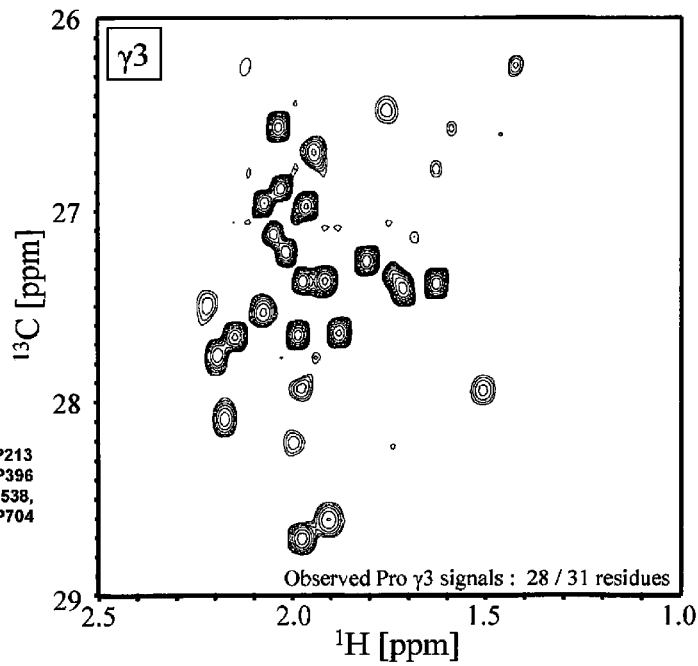
Observed Pro γ3 signals : 28 / 31 residues

STABLE ISOTOPE-LABELED ALIPHATIC AMINO ACID AND NMR STRUCTURAL ANALYSIS OF PROTEIN USING SAME

CROSS-REFERENCE TO RELATED APPLICATIONS

This application is a U.S. National Stage filing under 35 U.S.C. §371 of International Application No. PCT/JP2013/053901, filed Feb. 18, 2013, which in turn claims priority to Japanese Patent Application No. 2012-180615, filed Aug. 16, 2012, the entire contents of which are incorporated by reference herein.

TECHNICAL FIELD

The present invention relates to a stable isotope-labeled aliphatic amino acid suitable for use in a structural analysis method for a protein according to an NMR technique, a composition containing the stable isotope-labeled aliphatic amino acid, a method for incorporating the stable isotope-labeled aliphatic amino acid into a protein, and an NMR structural analysis method for a protein.

BACKGROUND ART

It is widely known that biological functions of a variety of proteins are each expressed when a peptide chain having a primary sequence of amino acids intrinsic to each protein forms a unique three-dimensional structure according to the primary sequence of the amino acids. Hence, information on three-dimensional structures of proteins are quite important intellectual properties, and collected in an international information collecting institution (Protein Data Bank (hereinafter may also be referred to as PDB); for example, see, "RCSB Protein data bank", [online], the Research Collaboratory for Structural Bioinformatics, [retrieved on Heisei 24.7.25 (Jul. 25, 2012)], Internet (http://www.pdb.org/pdb/home/home.do)) and so forth. It is widely used in medicine, biology, and other basic researches, and in drug development and other applied researches.

Currently, the most potent method as an experimental approach for determining the three-dimensional structure of a protein is X-ray crystallography that utilizes an X-ray diffraction of a single crystal of a protein. Not less than 90% of information on three-dimensional structures of proteins collected every year in PDB are obtained from this X-ray crystallography.

On the other hand, an NMR technique which is a novel protein structure determination approach having been introduced in 1980s accounts for only 10% or less of information on three-dimensional structures provided to PDB and so forth until now. Nevertheless, this method is capable of determining the structure of a protein not in a crystallized state but in such a state that amino acid residues in the protein can freely move around in an environment similar to an environment where the protein plays its biological function, such as in an aqueous solution, micelle, and lipid bilayer. Since the method can provide so-called "dynamic structural information," there is information provided entirely different from "static structural information" generally obtained by the X-ray crystallography.

As described above, to be able to utilize dynamic structural information in addition to static structural information is a great advantage in making use of information on the three-dimensional structure of a protein in basic researches and applied researches. Hence, the development of novel NMR analysis techniques has attracted great interest worldwide, and various technical innovation competitions are taking place all over the world.

In this respect, the X-ray crystallography has already had satisfactory results as a structural analysis method for almost half a century and has been technically matured. On the other hand, only 20 years have passed since the NMR technique was introduced as a structural analysis method and the NMR technique still has a lot of problems to be solved. Among such problems, a problem sought to be solved as soon as possible is that proteins successfully subjected to structural analysis according to the NMR technique are limited to proteins having relatively low molecular weights.

In fact, the molecular weight of proteins whose structures have been specified by the NMR technique and registered in PDB is roughly 10,000 to 20,000. To solve such a problem in the present situation, technical improvements have been made in each of three basic technical fields such as (1) preparation technique of a protein sample labeled with a stable isotope, (2) multi-dimensional, multi-nuclear NMR measurement technique, and (3) three-dimensional structural analysis technique utilizing NMR spectrum information. Recently, a three-dimensional structure of a protein having a molecular weight of approximately 20,000 to 25,000 has also been successfully determined by utilizing NMR techniques. However, all of the NMR techniques utilizing the improved techniques so far are based on the premise that the structural analysis precision is sacrificed to some extent in order to determine the structure of a protein having a higher molecular weight. For this reason, regarding information on the three-dimensional structure of a high-molecular-weight protein obtained by an NMR technique utilizing conventional techniques, the precision of the structural analysis is insufficient, and such a precision problem in the structural analysis has been a major obstacle when obtained information on a three-dimensional structure is utilized in the fields of drug development and the like.

The present inventors have already demonstrated that developing a method for optimizing a technique associated with all of the above basic technical fields (1) to (3) makes it possible to develop a technique enabling a structural analysis at a level far higher than the molecular-weight limitation in the NMR technique, and also to achieve a great improvement in the precision of a structural analysis and a great reduction in the analysis time (see International Publication No. WO2003/053910). This novel technique later designated as the SAIL (Stereo-array isotope labeling) method by the present inventors has made it possible, as an innovative new technique, to increase the range of the molecular weight that can be successfully subjected to NMR structure analysis to a range of approximately 40,000 to 50,000, and simultaneously to increase the precision of the structural analysis. The basic idea of the SAIL method is to greatly reduce the number of hydrogen atoms ($^1$H) in amino acid residues constituting a protein without reducing the amount of information on a three-dimensional structure to be obtained, so that the structural information is obtained quickly with higher precision. Recently, a Canadian NMR research group has reported that, among amino acid residues forming a hydrophobic core of a protein, selectively forming only methyl groups of leucine (Leu), valine (Val), and isoleucine (Ile) as $^{13}C^1H_3$ and deuterating all the remaining hydrogen atoms make it possible to observe sharp NMR signals of the methyl groups of these amino acid residues even in a high-molecular-weight protein having a molecular weight exceeding 100 kDa, and to determine a fold structure of a peptide chain of the protein. Although the precision of obtained structural information is insufficient, this approach makes it possible to prepare a sample easily by utilizing readily available methyl-labeled amino acids described above, and to apply an NMR technique to proteins having high molecular weights, which has been thought to be impossible heretofore. Accordingly, the application of this approach is increasing as an innovative technique.

On the other hand, in International Publication No. WO2007/099934, the present inventors have developed stable isotope-labeled amino acids for more reliable and higher sensitivity assignment of $^{13}C$ and $^1H$ signals of amino acid residue side chains. In these stable isotope-labeled amino acids, a methylene proton ($^1H$) on a side chain is isolated by deuterating a neighboring hydrogen atom, thereby enabling high sensitivity observation of an NMR signal derived from the methylene proton. Simultaneously, signal assignment can be easily achieved by spin couplings of 3J ($^{13}C$—$^{13}C$), 3J ($^{13}C$—$^1H$), or the like.

SUMMARY OF INVENTION

Technical Problems

However, when the invention of International Publication No. WO2007/099934 is used, the presence of a $^{13}C$—$^{13}C$ bond in a high-molecular-weight protein having a molecular weight exceeding 80 kDa requires that a constant time evolution technique be utilized in the NMR spectrum measurement. As a result, the sensitivity and precision of NMR spectra are greatly reduced, which makes analyses such as sequential assignment significantly difficult.

Accordingly, the present invention provides a stable isotope-labeled aliphatic amino acid enabling the assignment of the signal of an amino acid residue side chain by increasing to the maximum the observation sensitivity to an NMR signal of the same amino acid residue side chain, and allowing NOE (nuclear Overhauser effect) between protons in the amino acid residue to be observed. Specifically, the present invention provides a novel stable isotope-labeled aliphatic amino acid enabling stereospecific assignment of a methylene proton on a side chain of an over 80 kDa protein, and allowing detailed information on the structure of the high-molecular-weight protein to be obtained.

Solution to Problems

In view of the above-described problems, the inventors of the present invention have conducted earnest study. As a result, the inventors have found that the problems can be solved with a stable isotope-labeled aliphatic amino acid in which: two or more carbon atoms are labeled with $^{13}C$ in such a manner that the carbon atoms are not adjacent to each other; and, of two or more carbon atoms labeled with $^{13}C$, a carbon atom other than that of a methyl group, which is capable of bonding to a hydrogen atom, has one $^1H$ directly bonded thereto, while the carbon atom of the methyl group has at least one $^1H$ directly bonded thereto. This finding has led to the completion of the present invention.

Specifically, the present invention provides the following.

[1] A stable isotope-labeled aliphatic amino acid for constituting a protein, satisfying all of the following conditions (1) to (3):
(1) two or more carbon atoms are labeled with $^{13}C$;
(2) of two or more carbon atoms labeled with $^{13}C$, a carbon atom other than a carbon atom of a methyl group, which is capable of bonding to a hydrogen atom, has one $^1H$ directly bonded thereto, while the carbon atom of the methyl group has at least one $^1H$ directly bonded thereto; and
(3) other carbon atoms adjacent to all the $^{13}C$ are all $^{12}C$.

[2] The stable isotope-labeled aliphatic amino acid according to [1], wherein (4) the number of carbon atoms located between the $^{13}C$ having $^1H$ directly bonded thereto and another carbon atom having $^1H$ directly bonded thereto is three or less.

[3] The stable isotope-labeled aliphatic amino acid according to [2], wherein (5) the other carbon atom having $^1H$ directly bonded thereto is labeled with $^{13}C$.

[4] The stable isotope-labeled aliphatic amino acid according to any one of [1] to [3], wherein (6) a carbon atom of at least one methylene chain among methylene chains present at side chains of the amino acid is labeled with $^{13}C$, and one of two hydrogen atoms directly bonded to the $^{13}C$ is stereo-selectively labeled with $^2H$.

[5] The stable isotope-labeled aliphatic amino acid according to any one of [1] to [4], wherein (7) one of two hydrogen atoms directly bonded to a $^{12}C$ carbon atom of a methylene chain present at the side chain of the amino acid is labeled with $^2H$, or both of the two hydrogen atoms are $^1H$ or $^2H$.

[6] The stable isotope-labeled aliphatic amino acid according to any one of [1] to [5], wherein (8) in a case where pro-chiral gem-methyl groups are present, one of the gem-methyl groups is labeled with $^{12}C^2H_3$ or $^{13}C^2H_3$.

[7] The stable isotope-labeled aliphatic amino acid according to any one of [1] to [6], which is glutamic acid (Glu), isoleucine (Ile), lysine (Lys), leucine (Leu), methionine (Met), proline (Pro), glutamine (Gln), arginine (Arg), threonine (Thr), or valine (Val).

[8] The stable isotope-labeled aliphatic amino acid according to any one of [1] to [7], which is represented by one of the following ten structural formulas:

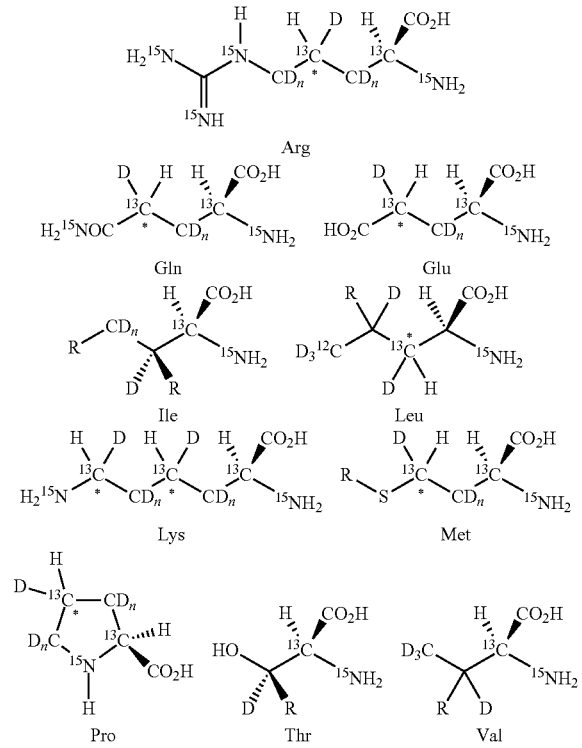

wherein R represents $^{13}C^1H_3$, $^{13}C^1H_2D$, or $^{13}C^1HD_2$, H has the same meaning as $^1H$, D has the same meaning as $^2H$, C has the same meaning as $^{12}C$, * represents a stereogenic center, the amino acids are any one of enantiomers with respect to the stereogenic center, n represents any one of 0 to 2, and in the case where n is 1, the amino acid may be a racemate or any one of enantiomers with respect to a carbon atom to which the corresponding deuterium is bonded.

[9] The stable isotope-labeled aliphatic amino acid according to any one of [1] to [7], which is represented by one of the following ten structural formulas:

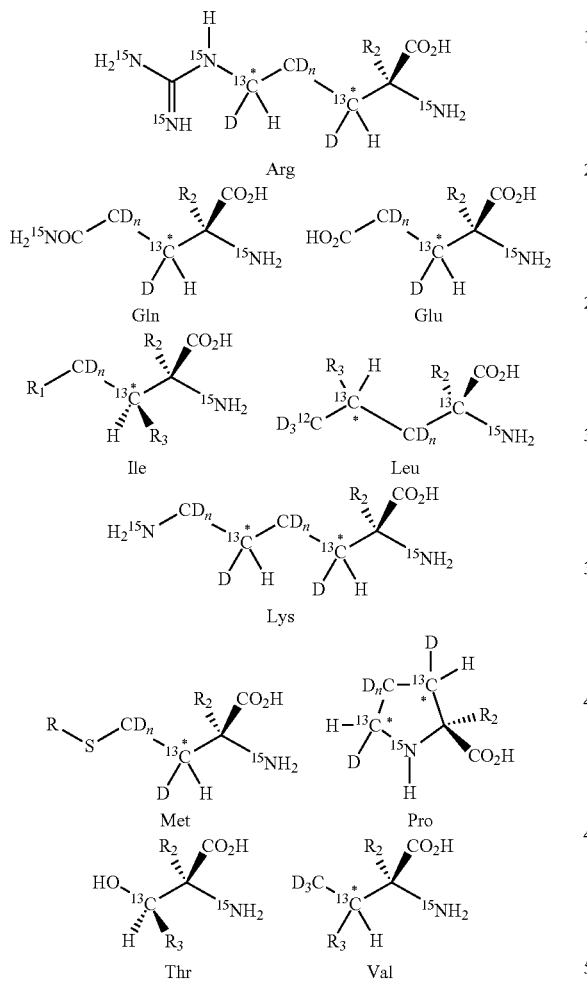

wherein R represents $^{13}C^1H_3$, $^{13}C^1H_2D$, or $^{13}C^1HD_2$, $R_2$ represents $^1H$ or $^2H$, $R_3$ represents $^{12}C^1H_3$, $^{12}C^1H_2D$, or $C^1HD_2$, H has the same meaning as $^1H$, D has the same meaning as $^2H$, C has the same meaning as $^{12}C$, * represents a stereogenic center, the amino acids are any one of enantiomers with respect to the stereogenic center, n represents any one of 0 to 2, and in the case where n is 1, the amino acid may be a racemate or any one of enantiomers with respect to a carbon atom to which the corresponding deuterium is bonded.

[10] A composition comprising at least one of the stable isotope-labeled aliphatic amino acids of the present invention.

[11] A composition comprising at least one of the stable isotope-labeled aliphatic amino acids according to [8] or [9], which further comprises at least one of stable isotope-labeled amino acids represented by one of the following nine structural formulas:

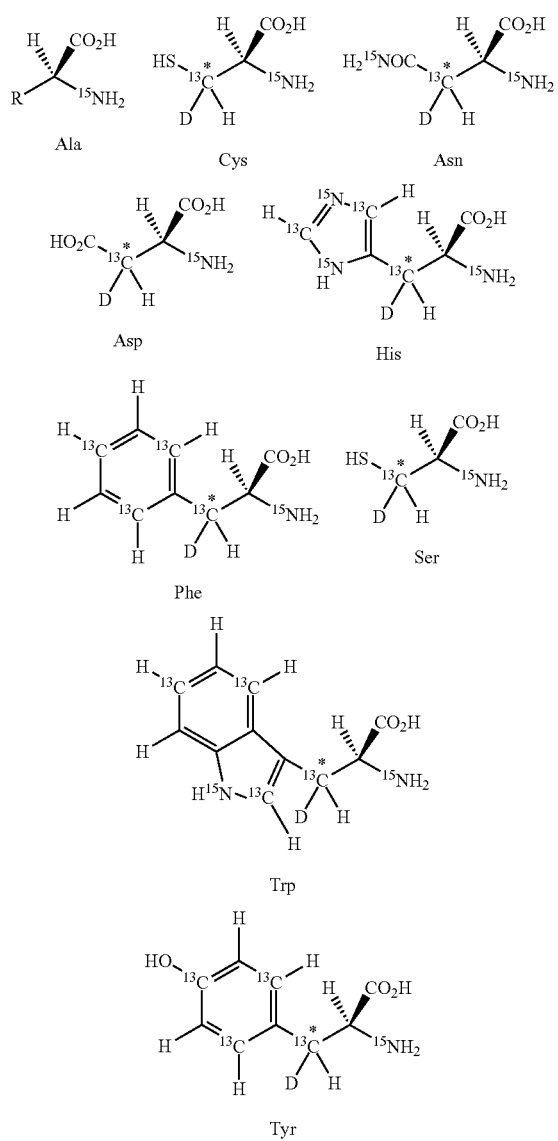

wherein R represents $^{13}C^1H_3$, $^{13}C^1H_2D$, or $^{13}C^1HD_2$, H has the same meaning as $^1H$, D has the same meaning as $^2H$, C has the same meaning as $^{12}C$, * represents a stereogenic center, and the amino acids are any one of enantiomers with respect to the stereogenic center.

[12] A method for incorporating a stable isotope-labeled aliphatic amino acid into a protein, comprising the step of synthesizing a protein using cultured cells, microorganisms, or a cell-free protein synthesis system in presence of the stable isotope-labeled aliphatic amino acid of the present invention.

[13] An NMR structural analysis method for a protein, comprising the step of measuring an NMR spectrum of a solution of a purified protein obtained by the method for incorporating a stable isotope-labeled aliphatic amino acid into a protein of the present invention.

Advantageous Effects of Invention

In the stable isotope-labeled aliphatic amino acid of the present invention, two or more carbon atoms are labeled with $^{13}C$ in such a manner that the carbon atoms are not adjacent to each other; of two or more carbon atoms labeled with $^{13}C$, a carbon atom other than that of a methyl group, which is capable of bonding to a hydrogen atom, has one $^1H$ directly bonded thereto, while the carbon atom of the methyl group has at least one $^1H$ directly bonded thereto. Accordingly, when the structure of the protein is analyzed according to an NMR technique, the observation sensitivity to NMR signals of amino acid residue side chains is sufficiently increased, and NOE between protons in the amino acid residue is allowed to be observed. Thereby, it is made possible to assign the signal of the amino acid residue side chains. This also makes it possible to analyze the three-dimensional structure of a methylene proton on a side chain of an over 80 kDa protein, which has been impossible heretofore, and allows detailed information on the structure of the high-molecular-weight protein to be obtained.

BRIEF DESCRIPTION OF DRAWINGS

FIG. 15 shows an NMR spectrum at the γ-position of the leucine residue of the [$^2H$; $^{15}N$]MSG incorporating Pro (3) that is the stable isotope-labeled proline of the present invention.

DESCRIPTION OF EMBODIMENTS

Figure 1:
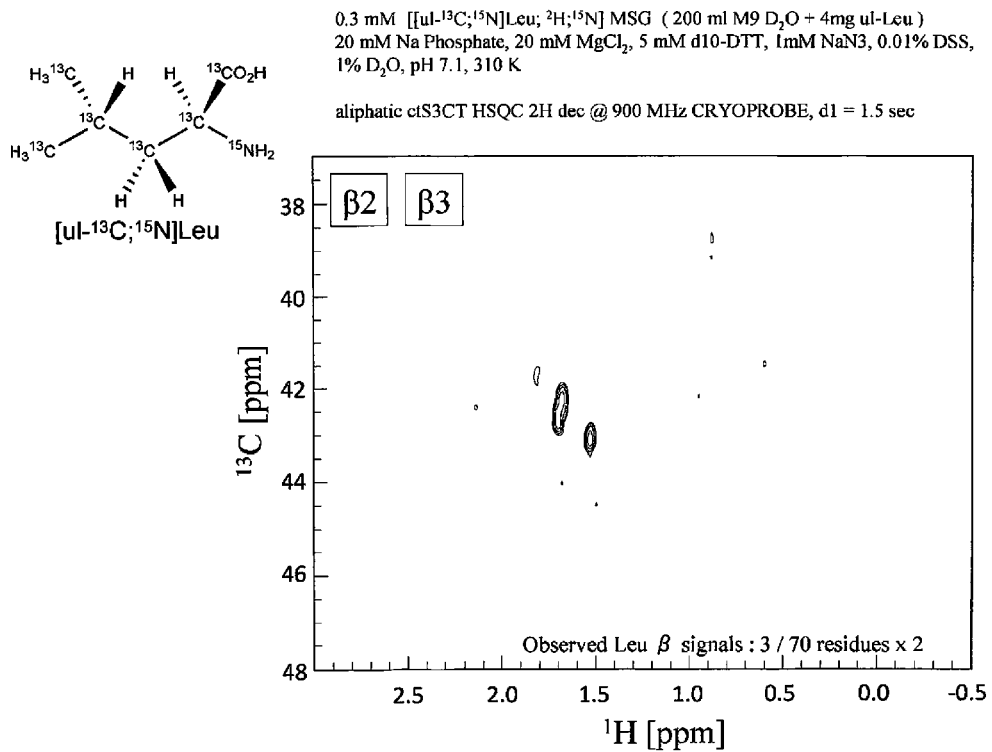
FIG. 1 shows an NMR spectrum at the β-position of a leucine residue of [$^2H$; $^{15}N$]MSG incorporating [ul-$^{13}C$; $^{15}N$]Leu.

Hereinafter, the present invention will be described in detail with reference to the drawings.

<Stable Isotope-Labeled Amino Acid>

A stable isotope-labeled aliphatic amino acid of the present invention satisfies all of the following conditions (1) to (3).

(1) two or more carbon atoms are labeled with $^{13}C$;

(2) of two or more carbon atoms labeled with $^{13}C$, a carbon atom other than a carbon atom of a methyl group, which is capable of bonding to a hydrogen atom, has one $^1H$ directly bonded thereto, while the carbon atom of the methyl group has at least one $^1H$ directly bonded thereto; and (3) other carbon atoms adjacent to all the $^{13}C$ are all $^{12}C$.

When the structure of a protein is analyzed according to an NMR technique, the observation sensitivity to NMR signals of amino acid residues is sufficiently increased by using the stable isotope-labeled aliphatic amino acid of the present invention, and NOE between protons in the amino acid residue is allowed to be observed. Thereby, it is made possible to assign the signal of amino acid residue side chains. This also makes it possible to analyze the three-dimensional structure of a methylene proton on a side chain of an over 80 kDa protein, which has been impossible heretofore, and allows detailed information on the structure of the high-molecular-weight protein to be obtained.

To be more specific, the stable isotope-labeled aliphatic amino acid of the present invention satisfying the conditions (1) and (3) makes it possible to avoid a complication of $^{13}C$ signals due to spin couplings. Conventionally known methods including methods described in International Publication No. WO2003/053910 and 2 utilize $^{13}C$—$^{13}C$ spin couplings for assignment of $^{13}C$ signals derived from a stable isotope-labeled aliphatic amino acid. Accordingly, it has been necessary to avoid a complication in a spectrum by employing a constant time evolution technique that is an approach sacrificing the sensitivity and resolution of an NMR spectrum. In contrast, the stable isotope-labeled aliphatic amino acid satisfying the conditions (1) and (3) makes it possible to avoid a complication of $^{13}C$ signals derived from the stable isotope-labeled aliphatic amino acid without employing the constant time evolution technique. Thus, an NMR structural analysis method can be performed with high sensitivity and high resolution even on a protein having a higher molecular weight.

Moreover, since the stable isotope-labeled aliphatic amino acid of the present invention satisfies the conditions (2), the information on the three-dimensional structure determined by the assignment of $^1H$ signals utilizing NOE is maintained, and also $^1H$ does not excessively remain in a side chain of the stable isotope-labeled aliphatic amino acid. Thus, it is possible to avoid the broadening of a $^1H$-derived signal due to a dipole interaction. Hence, an NMR structural analysis can be performed with high sensitivity and high resolution even on a protein having a higher molecular weight.

In other words, in the present invention, $^1$H bonding to $^{13}$C is isolated from the other $^{13}$C—$^1$H in the amino acid. This makes it possible to prevent a complication of the $^1$H NMR signal, and to observe a signal derived from $^{13}$C—$^1$H with high sensitivity and high resolution.

The stable isotope-labeled aliphatic amino acid of the present invention preferably further satisfies at least one or more conditions selected from the group consisting of the following conditions (4) to (8):

(4) the number of carbon atoms located between the $^{13}$C having $^1$H directly bonded thereto and another carbon atom having $^1$H directly bonded thereto is three or less;

(5) under the condition (4), the other carbon atom having $^1$H directly bonded thereto is labeled with $^{13}$C;

(6) a carbon atom of at least one methylene chain among methylene chains present at side chains of the amino acid is labeled with $^{13}$C, and one of two hydrogen atoms directly bonded to the $^{13}$C is stereo-selectively labeled with $^2$H;

(7) one of two hydrogen atoms directly bonded to a $^{12}$C carbon atom of a methylene chain present at the side chain of the amino acid is labeled with $^2$H, or both of the two hydrogen atoms are concurrently $^1$H or $^2$H; and (8) in a case where pro-chiral gem-methyl groups are present, one of the gem-methyl groups is labeled with $^{12}$C$^2$H$_3$ or $^{13}$C$^2$H$_3$.

Preferably, the stable isotope-labeled aliphatic amino acid of the present invention simultaneously satisfies the conditions (4) to (6) among any of these conditions.

The stable isotope-labeled aliphatic amino acid of the present invention satisfying the condition (4) facilitates assignment of $^1$H signals by utilizing NOE observed between multiple $^1$Hs, and facilitates assignment of structures of amino acid residues in a protein without utilizing a sequential assignment technique having been conventionally performed.

Moreover, the stable isotope-labeled aliphatic amino acid of the present invention satisfying the condition (5) further facilitates assignment of $^1$H signals by utilizing NOE observed between multiple $^1$Hs, and further facilitates assignment of structures of amino acid residues in a protein without utilizing the sequential assignment technique having been conventionally performed.

The stable isotope-labeled aliphatic amino acid of the present invention satisfying the condition (6) makes it possible to simplify a signal derived from $^{13}$C—$^1$H, and also enables stereospecific assignment of the entire —$^{13}$C$^1$H$^2$H— because $^1$H is stereo-selectively bonded to the $^{13}$C.

Furthermore, the stable isotope-labeled aliphatic amino acid of the present invention satisfying the condition (7) makes it possible, in the case where the two hydrogen atoms bonded to the $^{12}$C are labeled with $^2$H, to simplify a signal of the $^1$H bonded to the other carbon atom; meanwhile, in the case where at least one of the hydrogen atoms bonded to the $^{12}$C is $^1$H, NOE observed between this $^1$H and the $^1$H bonded to the other carbon atom enables assignment of structures of amino acid residues in a protein.

Furthermore, the stable isotope-labeled aliphatic amino acid of the present invention satisfying the condition (8) makes it possible to reduce the number of signals from methyl groups, accordingly making it possible to avoid a complication of the signals.

The stable isotope aliphatic amino acid is not particularly limited, as long as the aliphatic amino acid satisfies the conditions (1) to (3) and constitutes a protein. Nevertheless, the aliphatic amino acid is preferably glutamic acid (Glu), isoleucine (Ile), lysine (Lys), leucine (Leu), methionine (Met), proline (Pro), glutamine (Gln), arginine (Arg), threonine (Thr), or valine (Val).

More specifically, the stable isotope-labeled aliphatic amino acid of the present invention is preferably represented by one of the following ten structural formulas:

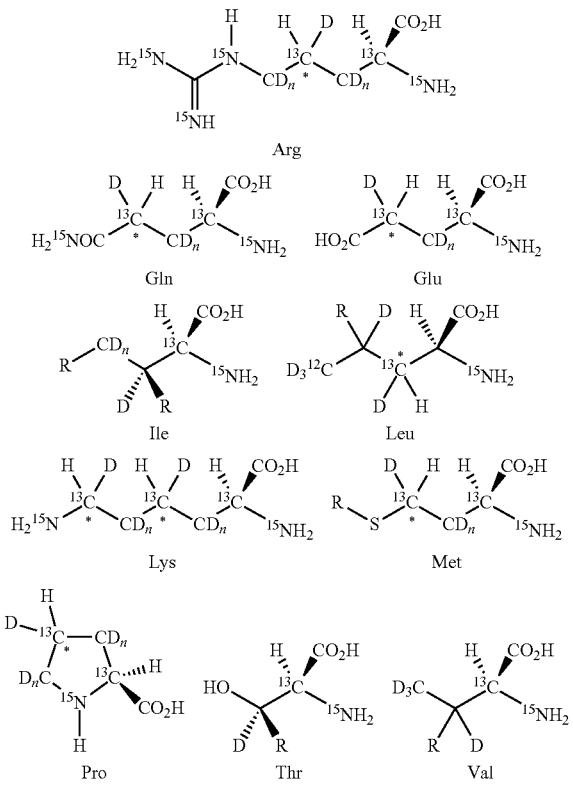

where R represents $^{13}$C$^1$H$_3$, $^{13}$C$^1$H$_2$D, or $^{13}$C$^1$HD$_2$, H has the same meaning as $^1$H, D has the same meaning as $^2$H, C has the same meaning as $^{12}$C, * represents a stereogenic center, the amino acids are any one of enantiomers with respect to the stereogenic center, n represents any one of 0 to 2, and in the case where n is 1, the amino acid may be a racemate or anyone of enantiomers with respect to a carbon atom to which the corresponding deuterium is bonded.

Further, the stable isotope-labeled aliphatic amino acid of the present invention is more preferably represented by one of the following ten structural formulas:

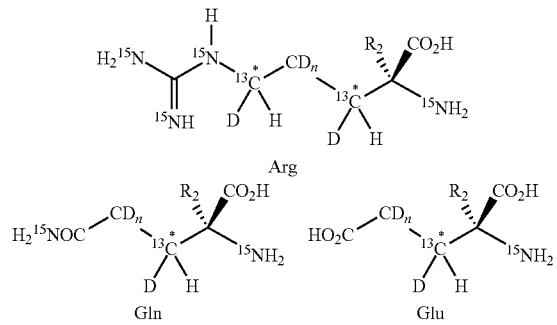

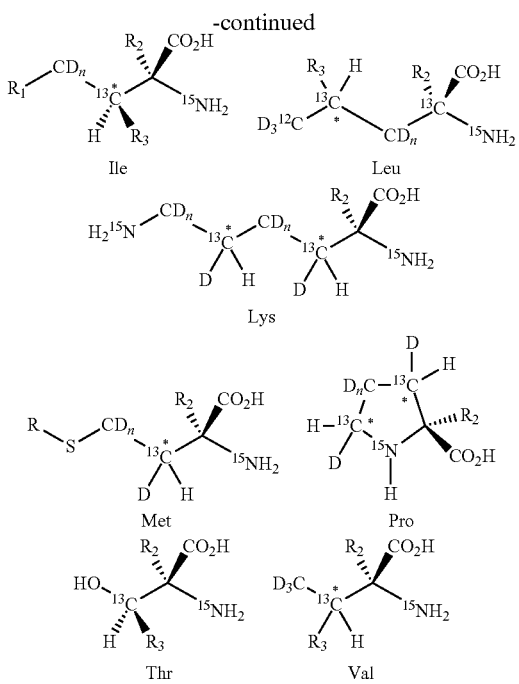

where R represents $^{13}C^1H_3$, $^{13}C^1H_2D$, or $^{13}C^1HD_2$, $R_2$ represents $^1H$ or $^2H$, $R_3$ represents $^{12}C^1H_3$, $^{12}C^1H_2D$, or $^{12}C^1HD_2$, H has the same meaning as $^1H$, D has the same meaning as $^2H$, C has the same meaning as $^{12}C$, * represents a stereogenic center, the amino acids are any one of enantiomers with respect to the stereogenic center, n represents any one of 0 to 2, and in the case where n is 1, the amino acid may be a racemate or any one of enantiomers with respect to a carbon atom to which the corresponding deuterium is bonded.

These stable isotope-labeled aliphatic amino acids can be prepared by employing a conventionally known preparation method and using reaction raw materials specifically labeled with $^{13}C$ and $^2H$ in accordance with isotope-labeled sites in the aliphatic amino acid. Specifically, the stable isotope-labeled aliphatic amino acid of the present invention can be prepared, for example, according to the method for preparing an amino acid described in International Publication No. WO2003/053910. Regarding the stable isotope-labeled reaction raw materials to be used, reaction raw materials and so forth (for example, "Acetic acid-2-13C", "Acetic acid-1-13C", "deuterium oxide", "Deuterium", "Glycine-2-13C, 15N") marketed from Taiyo Nippon Sanso Corporation or the like may be used. Furthermore, the stable isotope-labeled aliphatic amino acid of the present invention may be prepared according to methods for preparing an amino acid described in the following Literatures 1 to 4. Note that the content of International Publication No. WO2003/053910 is incorporated into the description of this specification by reference.

[Literature 1] Oba, M.; Ueno, R.; Fukuoka (nee Yoshida), M.; Kainosho, M.; Nishiyama, K., Synthesis of L-threo- and L-erythro-[1-$^{13}C$, 2,3-$^2H_2$]amino acids: novel probes for conformational analysis of peptide side chains., J. Chem. Soc., Perkin Trans. 1 1995, 1603.

[Literature 2] Terauchi, T.; Kamikawai, T.; Vinogradov, M. G.; Starodubtseva, E. V.; Takeda, M.; Kainosho, M. Synthesis of stereoarray isotope labeled (SAIL) lysine via the "head-to-tail" conversion of SAIL glutamic acid. Org. Lett., 2011, 13, 161-163.

[Literature 3] Okuma, K.; Ono, A. M.; Tsuchiya, S.; Oba, M.; Nishiyama, K.; Kainosho, M.; Terauchi, T. Assymetric synthesis of (2S,3R)- and (2S,3S)-[2-$^{13}C$; 3-$^2H$] glutamic acid. Tetrahedron Lett., 2009, 50, 1482-1484.

[Literature 4] Terauchi, T.; Kobayashi, K.; Okuma, K.; Oba, M.; Nishiyama, K.; Kainosho, M. Stereoselective synthesis of triply isotope-labeled Ser, Cys, and Ala: amino acids for stereoarray isotope labeling technology. Org. lett., 2008, 10, 2785-7.

<Composition Containing Stable Isotope-Labeled Amino Acid>

The present invention relates also to a composition containing the above-described stable isotope-labeled aliphatic amino acid. The composition of the present invention contains: at least one selected from the group consisting of the above-described stable isotope-labeled aliphatic amino acids; and a carrier. The combination and concentrations of the stable isotope-labeled aliphatic amino acids in the composition of the present invention may be adjusted appropriately depending on the purpose of use of the composition of the present invention.

Note that in a case where the composition of the present invention contains at least one selected from Arg, Gln, Glu, Ile, Leu, Lys, Met, Pro, Thr, and Val represented by the above-described 20 specific structural formulas as the stable isotope-labeled aliphatic amino acids, the composition of the present invention preferably further contains at least one of stable isotope-labeled amino acids represented by one of the following nine structural formulas:

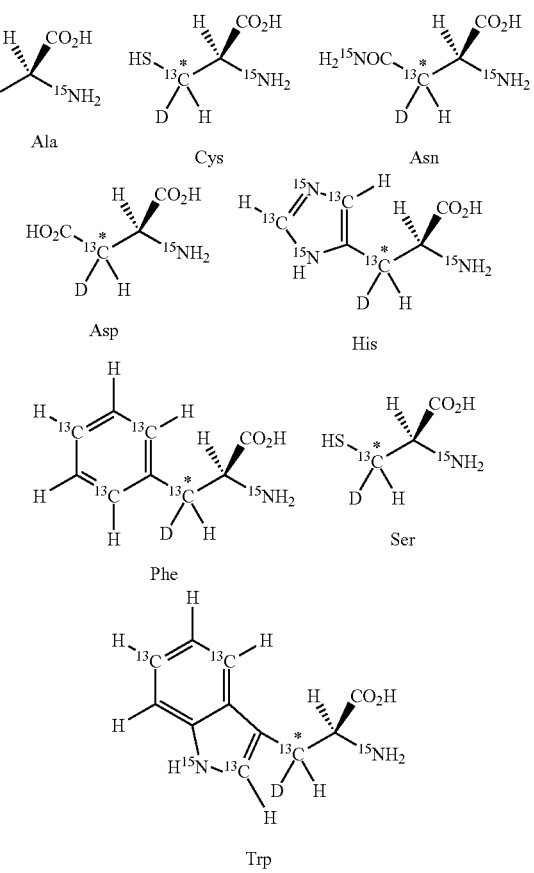

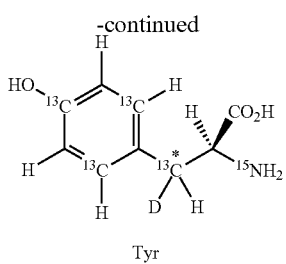

Tyr where R represents $^{13}C^1H_3$, $^{13}C^1H_2D$, or $^{13}C^1HD_2$, H has the same meaning as $^1H$, D has the same meaning as $^2H$, C has the same meaning as $^{12}C$, * represents a stereogenic center, and the amino acids are any one of enantiomers with respect to the stereogenic center.

<Method for Incorporating Stable Isotope-Labeled Amino Acid into Protein>

The present invention relates also to a method for incorporating the above-described stable isotope-labeled aliphatic amino acid into a protein. Here, the method for incorporating a stable isotope-labeled aliphatic amino acid into a protein of the present invention is a method including the step of synthesizing a protein using cultured cells, microorganisms, or a cell-free protein synthesis system in the presence of the above-described stable isotope-labeled aliphatic amino acid.

To be more specific, in the present invention, introduction of a gene fragment encoding a target protein whose structure is to be analyzed by an NMR technique into a system of the cultured cells, the microorganisms, the cell-free protein synthesis, or the like in such a manner that the gene fragment can be excessively expressed in these systems, and excessive expression of the protein in the presence of the stable isotope-labeled aliphatic amino acid are conducted to synthesize the protein, where a particular amino acid residue is replaced with an amino acid residue derived from the stable isotope-labeled aliphatic amino acid of the present invention.

The detailed conditions in performing such a method for incorporating a stable isotope-labeled aliphatic amino acid into a protein may be conditions designed in accordance with conventional methods for excessively expressing a protein using cultured cells, microorganisms, or a cell-free protein synthesis system.

<NMR Structural Analysis Method for Protein>

The present invention relates also to a method for an NMR structural analysis of a protein, including the step of measuring an NMR spectrum of a solution of a purified protein obtained by the above-described method for incorporating a stable isotope-labeled aliphatic amino acid into a protein. As the method for measuring an NMR spectrum, conventionally known approaches may be employed. In the NMR spectrum measurement, the protein may be bound to a conventionally known ligand and a different protein to measure the NMR spectrum in the state of a complex formed of the protein, the ligand, and the different protein.

The detailed conditions in performing these NMR structural analysis methods may be designed in accordance with conventional NMR structural analysis methods.

EXAMPLES

Hereinafter, the present invention will be described in detail based on Examples. Note that the present invention is not limited at all to Examples shown below.

<Synthesis of Stable Isotope-Labeled Leucine>

Two types of stable isotope-labeled leucines represented by chemical formulas 1 and 2 (hereinafter may be referred to as "Leu (1)" and "Leu (2)", respectively) were synthesized by a known synthesis method according to approaches described in the above [Literature 1] to [Literature 3] and the following [Literature 5]. The method for synthesizing each stable isotope-labeled leucine is shown below.

[Literature 5] Nahm, S.; Weinreb, S. M., N-Methoxy-N-methylamides as effective acylating agents. Tetrahedron Lett., 1981, 22, 38153818.

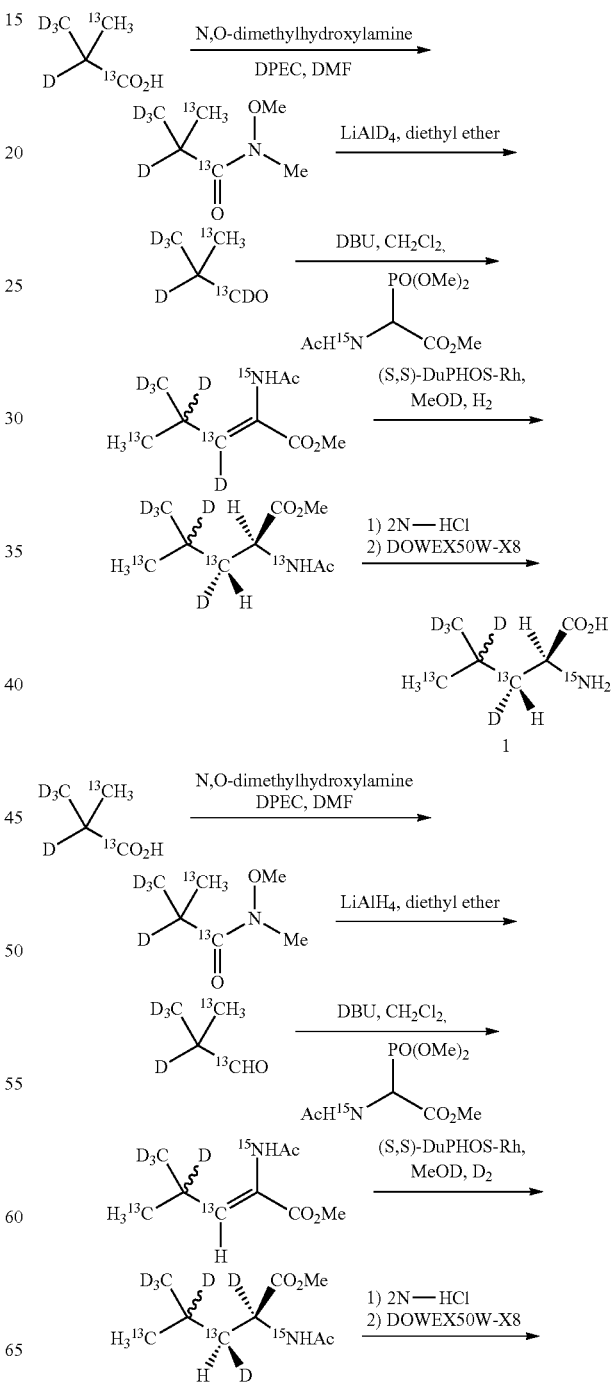

-continued

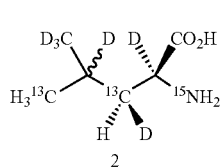

2

<Preparation of Proteins Incorporating Stable Isotope-Labeled Leucines>

Malate synthase G (molecular weight 82 kDa; hereinafter maybe referred to as "MSG") incorporating Leu (1) was prepared by a known approach according to the method in the following Literature 6. However, the leucine addition and culturing methods were modified as follows. After a plasmid MSG-pET28b having a DNA sequence encoding malate synthase G (MSG) was transformed into *Escherichia coli* BL21(DE3)pLysS strain, the transformed *Escherichia coli* was grown in an LB medium (2 ml) having been prepared using light water. The grown bacterial cells were collected and cultured at 37° C. for 20 hours in an M9 medium (3 ml) having been prepared using heavy water, in the presence of various vitamins. Then, the resultant was inoculated into a medium (100 ml) for main culturing in which Leu (1) (0.67 mg) had been dissolved, and cultured at 37° C. until the $OD_{600}$ reached approximately 0.3. To the resulting culture liquid, Leu (1) (1.33 mg) and IPTG (final concentration of 1 mM) were further added for MSG synthesis induction. After culturing at 37° C. for 8 hours, the bacterial cells were collected by centrifugation. By purifying a protein from the obtained bacterial cells with a known method according to the method in Literature 6, [Leu (1); $^2$H; $^{15}$N]MSG was obtained. [Leu (2); $^2$H; $^{15}$N]MSG was also prepared by employing the same approach as that for Leu (1).

[Literature 6] Tugarinov V, Muhandiram R, Ayed A, Kay L E, Four-dimensional NMR spectroscopy of a 723-residue protein: Chemical shift assignments and secondary structure of malate synthase G. J Am Chem Soc, 2002, 124: 10025-10035.

<Structural Analysis by NMR Technique>

Figure 2:
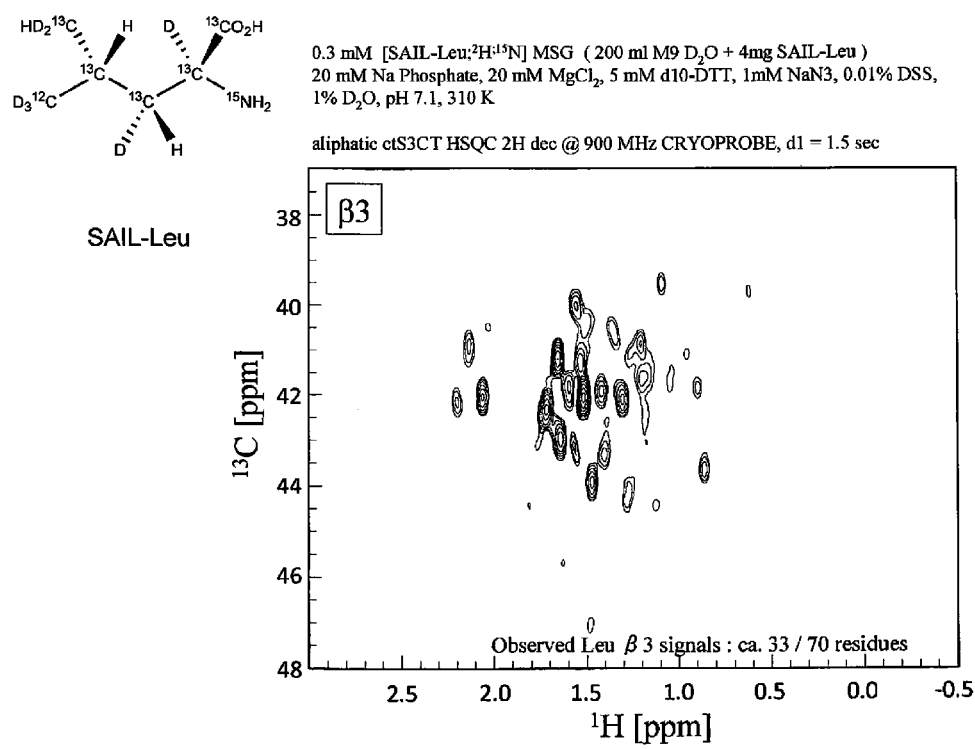
FIG. 2 shows an NMR spectrum at the β-position of a leucine residue of [$^2H$; $^{15}N$]MSG incorporating SAIL-Leu.
Figure 3:
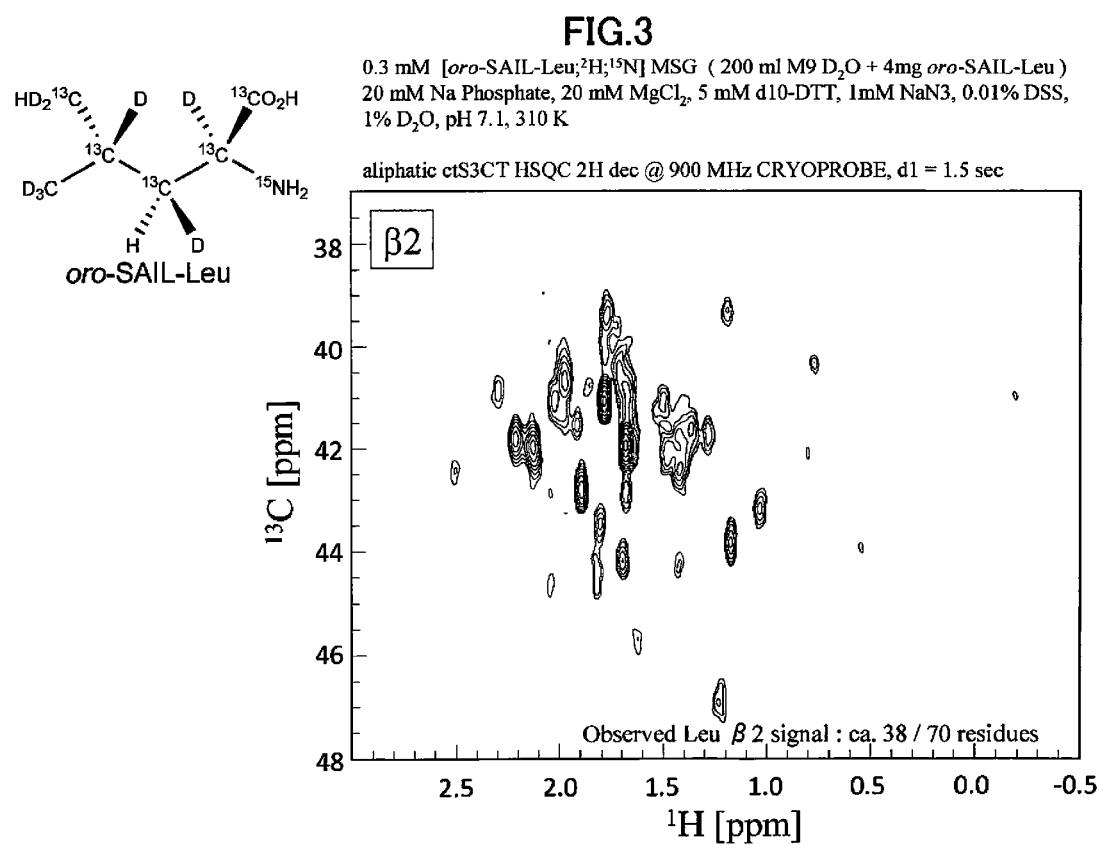
FIG. 3 shows an NMR spectrum at the β-position of leucine of [$^2H$; $^{15}N$]MSG incorporating oro-SAIL-Leu.
Figure 4:
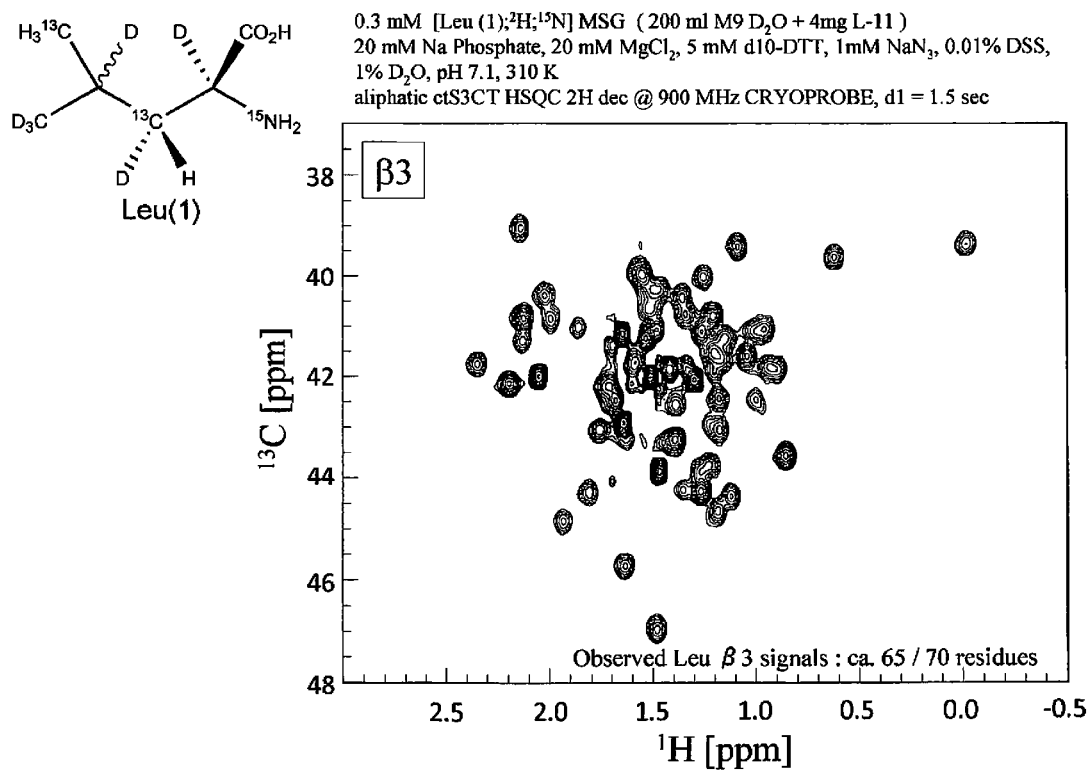
FIG. 4 shows an NMR spectrum at the β-position of a leucine residue of [$^2H$; $^{15}N$]MSG incorporating Leu (1) that is stable isotope-labeled leucine of the present invention.
Figure 5:
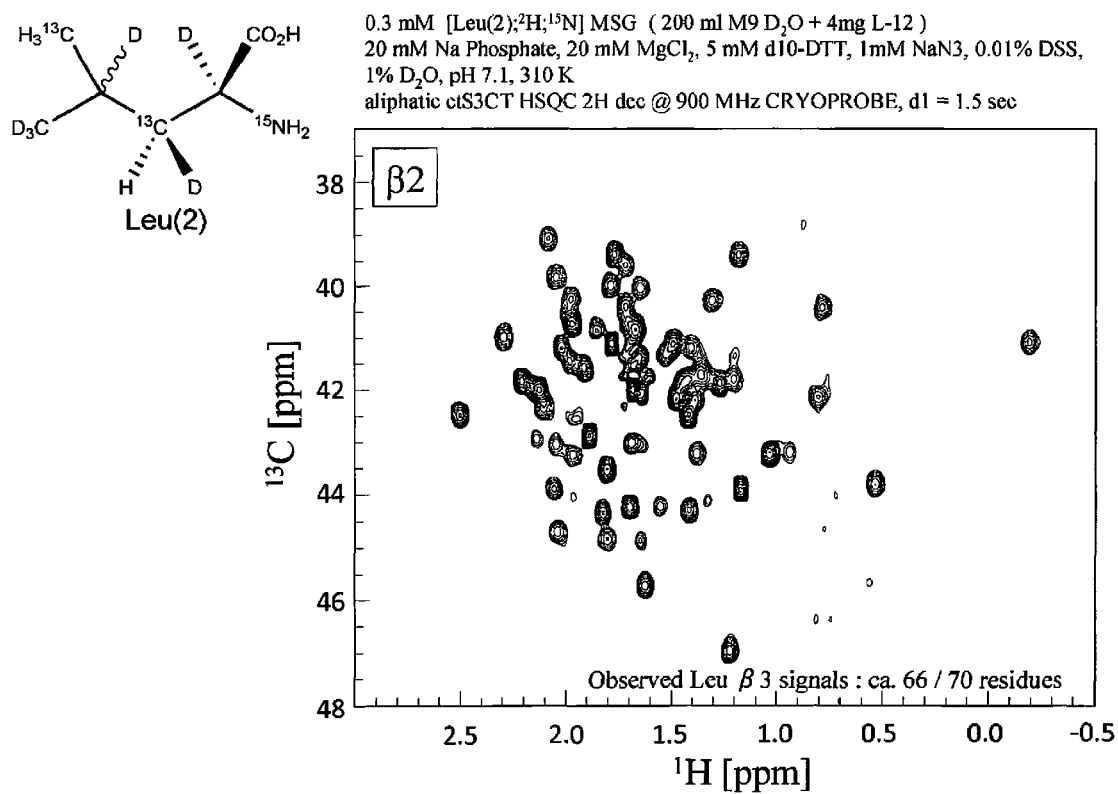
FIG. 5 shows an NMR spectrum at the β-position of a leucine residue of [$^2H$; $^{15}N$]MSG incorporating Leu (2) that is stable isotope-labeled leucine of the present invention.

To compare the NMR structural analysis method of the present invention with conventional methods, CT TROSY-HSQC of the [$^2$H; $^{15}$N]MSGs, which were prepared by using [ul-$^{13}$C; $^{15}$N] Leu whose structure is shown in FIG. 1, SAIL-Leu whose structure is shown in FIG. 2, oro-SAIL-Leu whose structure is shown in FIG. 3, and Leu (1) and Leu (2), was measured (FIGS. 1 to 5). Hydrogen Hα in the samples was labeled with a deuterium atom through metabolism because of the culturing in heavy water. MSG is a high-molecular-weight protein consisting of 723 amino acid residues including 70 residues in respect of even leucine residues. In MSG incorporating [ul-$^{13}$C; $^{15}$N]Leu, 140 signals of the β-position were supposed to be observed, but in fact the signals were significantly broadened due to the influence of a relaxation phenomenon between adjacent $^{13}$C and $^1$H nuclei, so that the signals of the β-position were hardly observed (FIG. 1). Moreover, in SAIL-Leu, since one of β protons was deuterated, the measurement sensitivity was enhanced slightly in comparison with [ul-$^{13}$C; $^{15}$N]Leu. Nevertheless, signals of only 33 residues were observed out of the 70 residues (FIG. 2). Further, in oro-SAIL-Leu, because of the effect that all the hydrogens present at the vicinal positions of the β proton are deuterated, the number of observed signals of the β-position was increased in comparison with SAIL-Leu. However, still a sufficient sensitivity was not obtained due to the influence of a relaxation phenomenon between $^{13}$C nuclei, so that only 38 residues were observed out of the 70 residues (FIG. 3). On the other hand, in Leu (1) and Leu (2) that are the examples of the stable isotope-labeled aliphatic amino acid of the present invention, the carbon atom and the hydrogen atoms at the β-position and the δ-position were specifically labeled with $^{13}$C and $^2$H, and the relaxation influence has been eliminated as much as possible. As a result, it was possible to observe β proton-derived signals corresponding to 66 residues and 67 residues in the MSGs incorporating Leu (1) and Leu (2), respectively (FIGS. 4 and 5).

Figure 6:
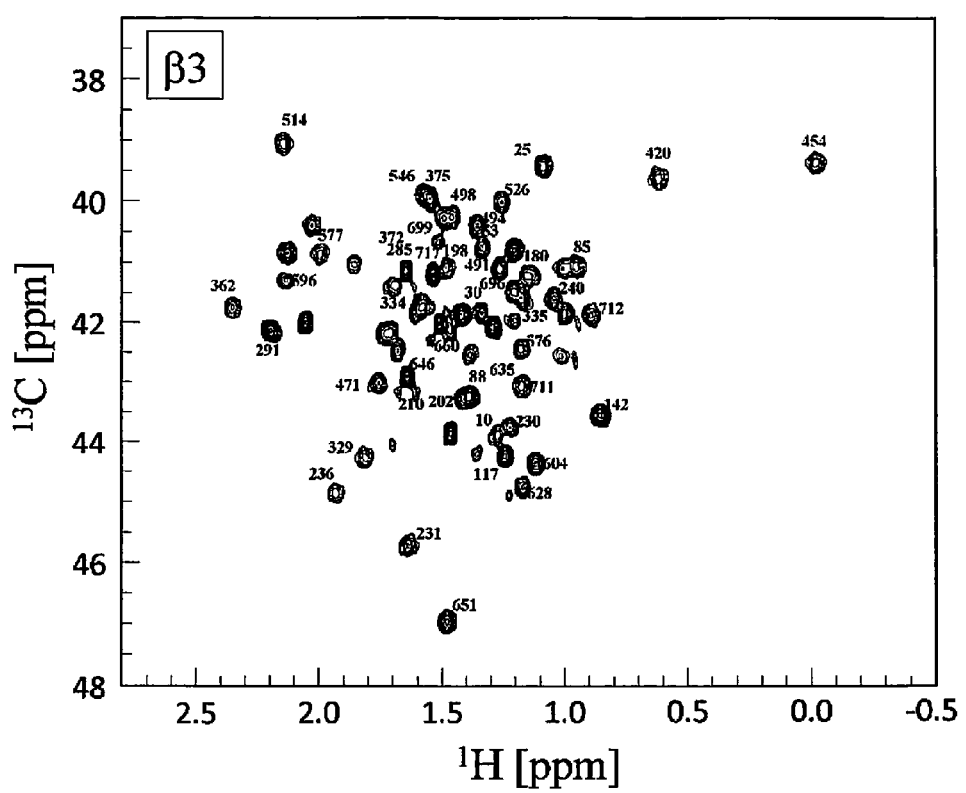
FIG. 6 shows a sequence-specific assignment of Hβ3 in the leucine residue of the [$^2H$; $^{15}N$]MSG incorporating Leu (1) that is the stable isotope-labeled leucine of the present invention.
Figure 7:
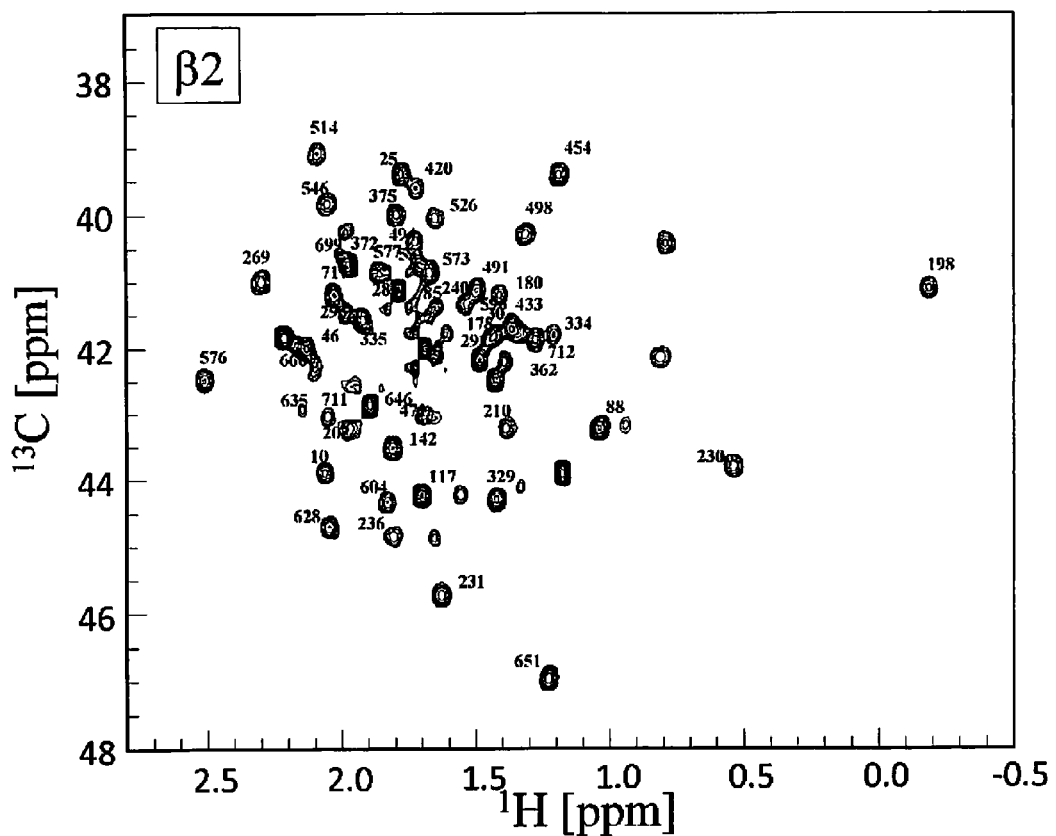
FIG. 7 shows a sequence-specific assignment of Hβ2 in the leucine residue of the [$^2H$; $^{15}N$]MSG incorporating Leu (2) that is the stable isotope-labeled leucine of the present invention.
Figure 8:
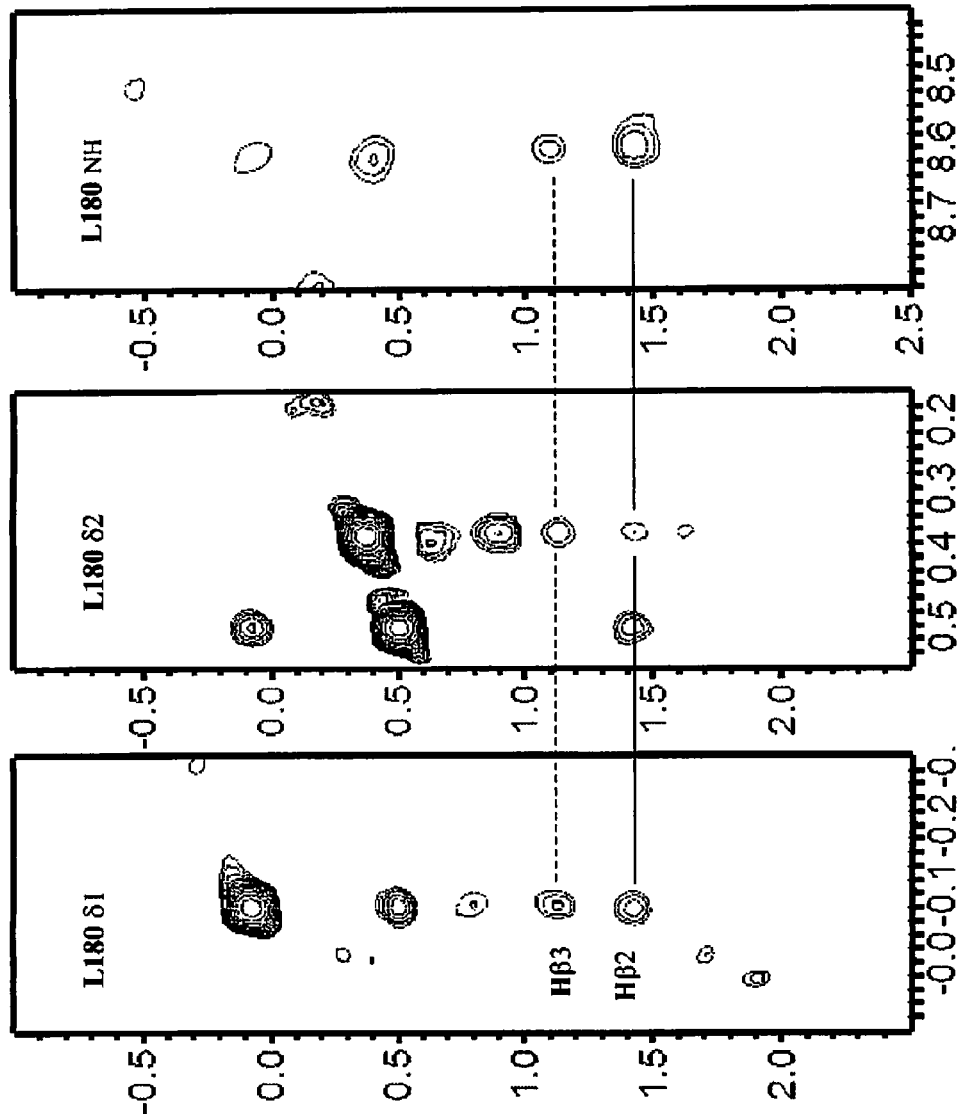
FIG. 8 shows NOE spectra between β2, β3 protons and a δ1 methyl proton (a), a δ2 methyl proton (b), or an amide proton (c) of L180 in the MSG.

It was found that utilizing Leu (1) and Leu (2) makes it possible to observe β protons stereospecifically with high sensitivity even in a high-molecular-weight protein (FIGS. 6 and 7). Further, analyzing NOE between a β proton and an amide proton or δ methyl proton in the amino acid residue makes it possible to easily determine sequence-specific sequential assignment and the conformation of Leu side chain. As an example, FIG. 8 shows NOE spectra in the 180th leucine (L180) residue of the MSG. It can be seen that although signals of β2 and β3 protons of L180 were observed from a δ1 methyl proton (FIG. 10*a*), a δ2 methyl proton (FIG. 10*b*) and an amide proton (FIG. 10*c*) of the L180, the relation of the signal intensity varied from one another. Specifically, it can be seen from this result that the distances from the δ1 methyl proton to the β2, β3 protons are approximately the same, but the β3 proton is located closer to the δ2 methyl proton than the β2 proton is. On the other hand, it can be seen that the β2 proton is located closer to the amide proton than the β3 proton is.

Figure 9:
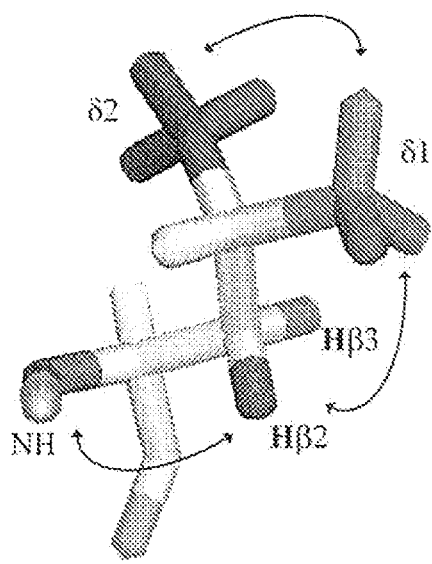
FIG. 9 shows the conformation of side chains of the L180 in the MSG.

These results revealed the relative arrangement of atomic groups of the L180, so that the conformation can be determined accurately (FIG. 9).

In this respect, Leu residues are generally present at an inner side of a protein, and form a core structure through a hydrophobic interaction with other amino acid residues in many cases. Thus, Leu residue-derived information is very useful in analyses of three-dimensional structures of proteins. Leu (1) and Leu (2) that are the examples of the stable isotope-labeled aliphatic amino acid of the present invention are capable of providing signals with high sensitivity even in a high-molecular-weight protein, and also providing information on conformation, accordingly showing a new way of a method for three-dimensional-structural analysis of high-molecular-weight proteins according to a solution NMR technique.

<Synthesis of Stable Isotope-Labeled Proline>

Stable isotope-labeled proline represented by chemical formula 3 (hereinafter may be referred to as Pro (3)) was synthesized by a known synthesis method according to approaches described in the following [Literature 7] to [Literature 9]. The method for synthesizing a stable isotope-labeled proline is shown below.

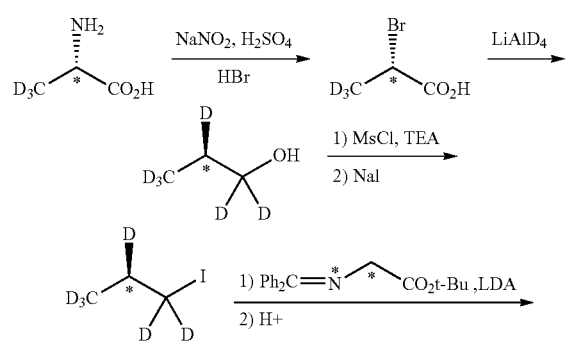

-continued

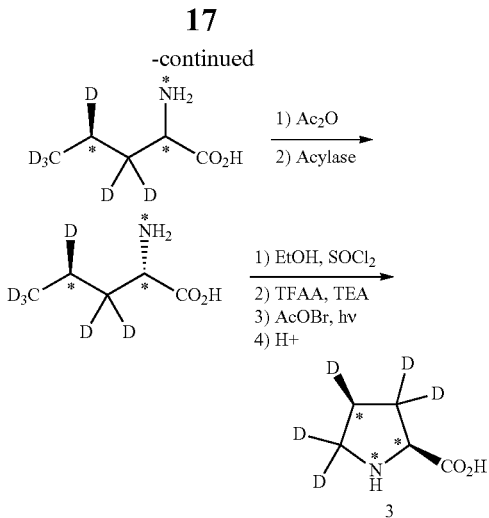

[Literature 7] Iida, K.; Kajiwara, M. J. Label. Compd. Radiopharm. 1991, 29, 201.

[Literature 8] Kajiwara, M.; Lee, S.-F.; Scott, A. I.; Akhtar, M.; Jones, C. R.; Jordan, P. M. Chem. Commun. 1978, 967.

[Literature 9] Reddy, L. R.; Reddy, B. V. S.; Corey, E. J. Org. lett., 2006, 8, 2819.

<Preparation of Protein Incorporating Stable Isotope-Labeled Proline>

Malate synthase G (MSG) using the stable isotope-labeled proline Pro (3) was prepared in accordance with the method in Literature 6. However, the methods for adding and culturing the stable isotope-labeled proline Pro (3) were modified as follows. After a plasmid MSG-pET28b was introduced into *E. coli* BL21 (DE3) pLysS strain, the resultant was grown in an LB medium (2 ml) having been prepared using light water. The grown bacterial cells were cultured at 37° C. for 20 hours in an M9 medium (3 ml) having been prepared using heavy water, in the presence of various vitamins. Then, the resultant was inoculated into a medium (100 ml) for main culturing in which the stable isotope-labeled proline (Pro (3), 1 mg) had been dissolved, and cultured at 37° C. until OD600=approximately 0.3. To the resulting medium, the stable isotope-labeled proline (Pro (3), 2 mg) and IPTG (final concentration of 1 mM) were added. After culturing at 37° C. for 8 hours, the bacterial cells were collected by centrifugation. By purifying a protein from the obtained bacterial cells in accordance with Literature 6, [Pro; $^2$H; $^{15}$N]MSG was obtained.

<Structural Analysis by NMR Technique>

Figure 10:
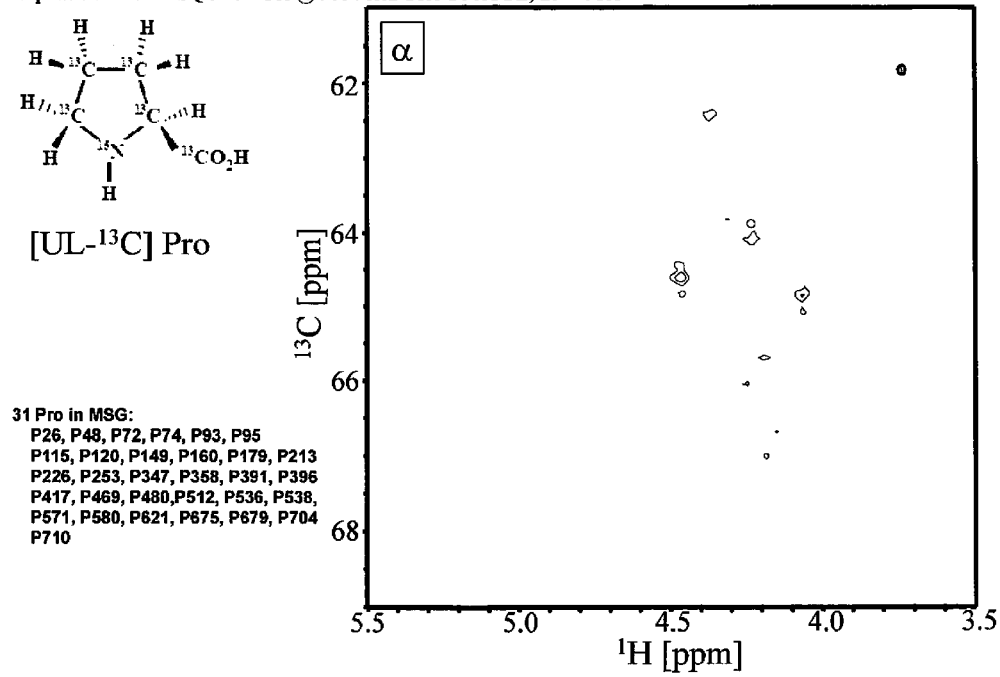
FIG. 10 shows an NMR spectrum at the α-position of a proline residue of [$^2H$; $^{15}N$]MSG incorporating [ul-$^{13}C$; $^{15}N$]Pro.
Figure 11:
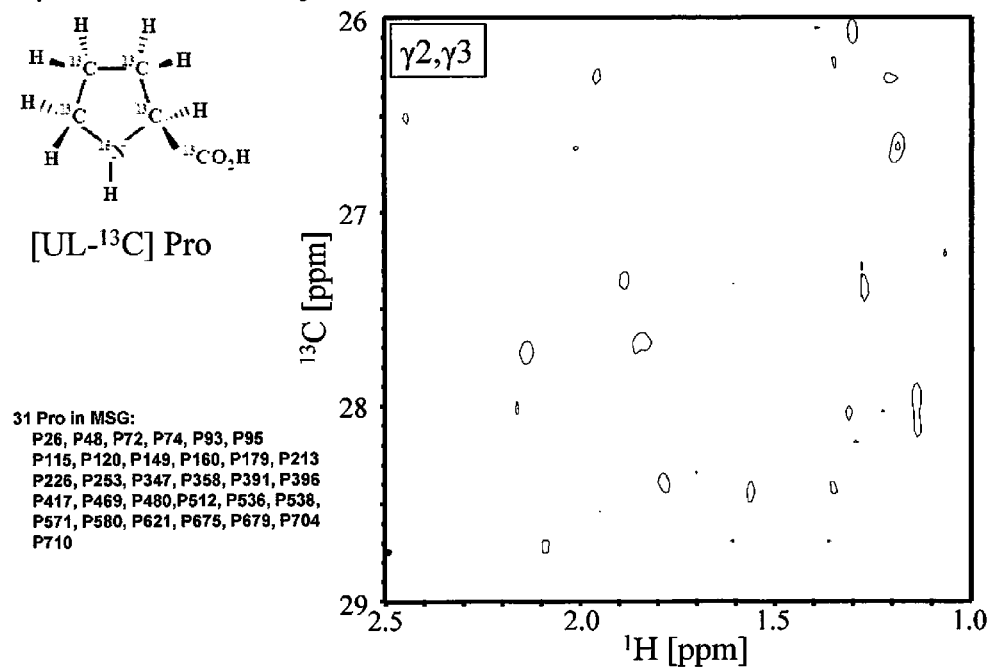
FIG. 11 shows an NMR spectrum at the γ-position of the proline residue of the [$^2H$; $^{15}N$]MSG incorporating [ul-$^{13}C$; $^{15}N$]Pro.
Figure 12:
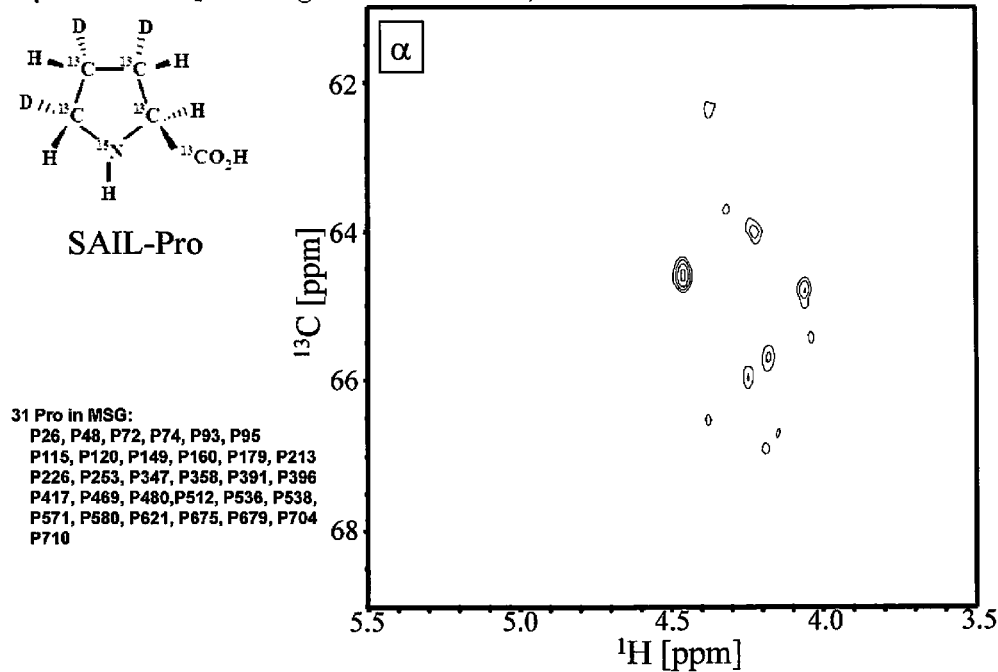
FIG. 12 shows an NMR spectrum at the α-position of a proline residue of [$^2H$; $^{15}N$]MSG incorporating SAIL-Pro.
Figure 13:
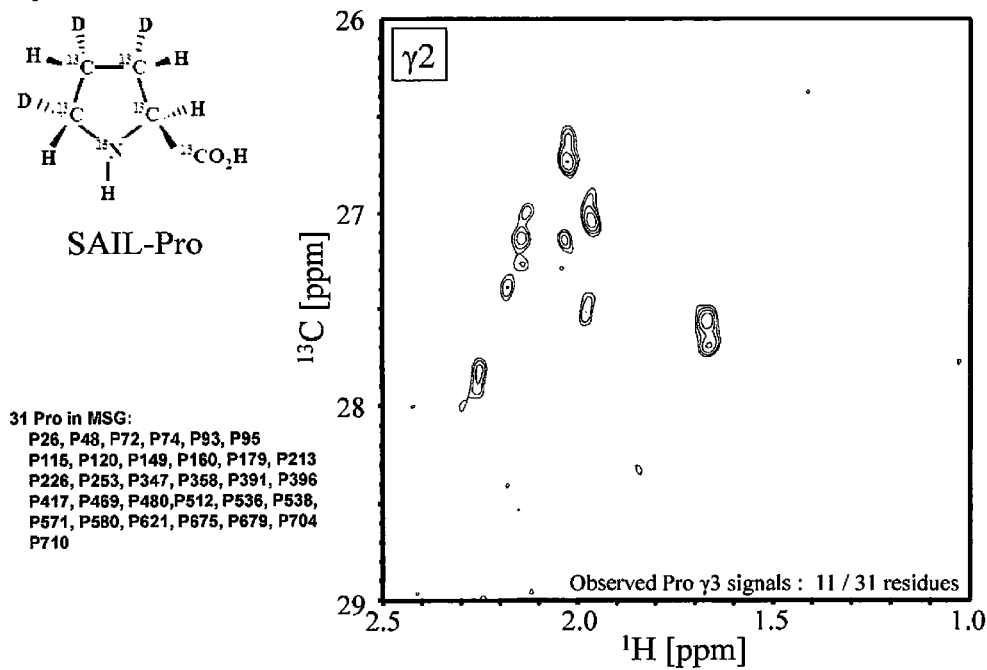
FIG. 13 shows an NMR spectrum at the γ-position of the proline residue of [$^2H$; $^{15}N$]MSG incorporating SAIL-Pro.
Figure 14:
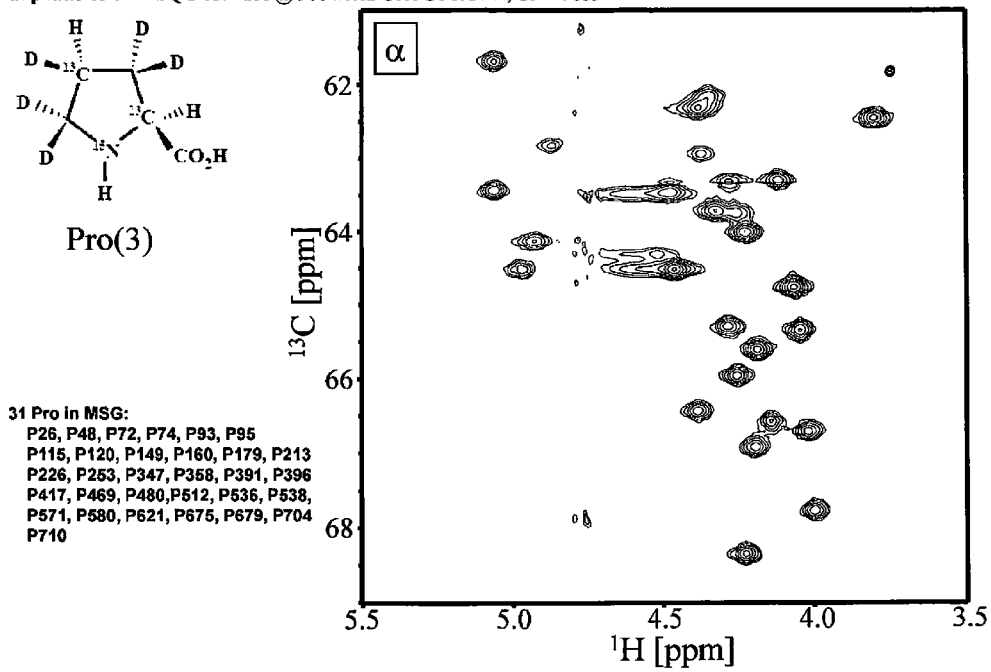
FIG. 14 shows an NMR spectrum at the α-position of a proline residue of [$^2H$; $^{15}N$]MSG incorporating Pro (3) that is stable isotope-labeled proline of the present invention.
Figure 16:
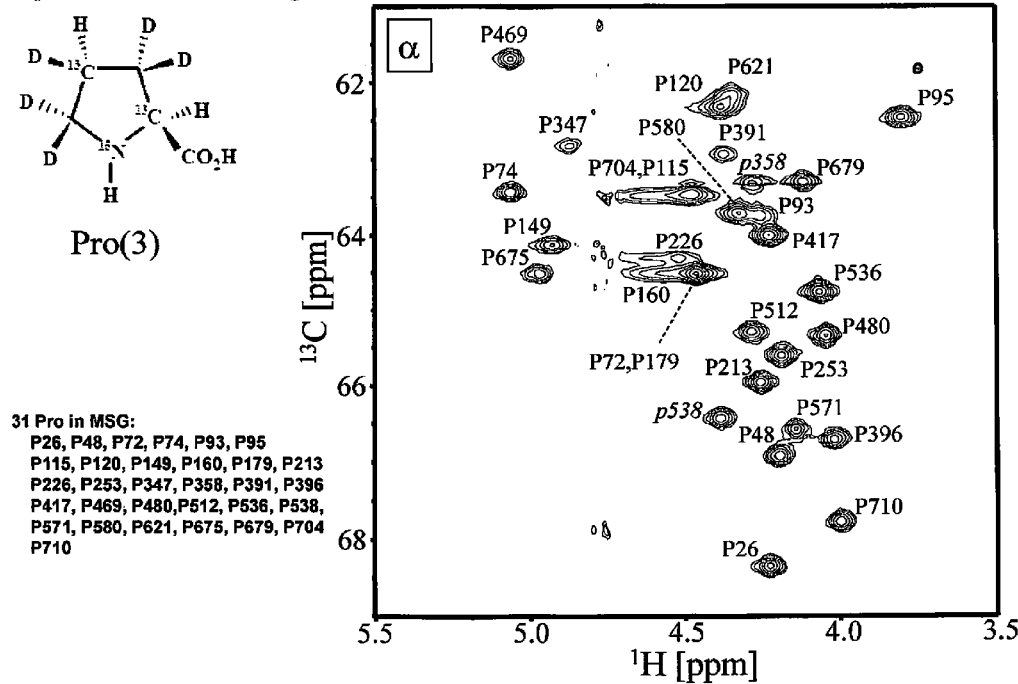
FIG. 16 shows sequence-specific assignment of Hα in the proline residue of the [$^2H$; $^{15}N$]MSG incorporating Pro (3) that is the stable isotope-labeled proline of the present invention.

For comparison with conventional methods, CT TROSY-HSQC of the [$^2$H; $^{15}$N]MSGs, which were prepared by using [ul-$^{13}$C; $^{15}$N]Pro whose structure is shown in FIGS. 10 and 11, SAIL-Pro whose structure is shown in FIGS. 12 and 13, and Pro (3) whose structure is shown in FIGS. 14 to 16. MSG is a high-molecular-weight protein consisting of 723 amino acid residues including 31 residues in respect of even proline residues. In MSG incorporating [ul-$^{13}$C; $^{15}$N]Pro, and 31 signals of the α-position and 62 signals of the γ-position were supposed to be observed, but actually the signals were significantly broadened due to the influence of a relaxation phenomenon between adjacent $^{13}$C and $^1$H nuclei, so that the signals were hardly observed (FIGS. 10 and 11). Moreover, in SAIL-Pro also, although one of protons on a side chain was deuterated as described above, a sufficient sensitivity was not obtained due to the influence of a relaxation phenomenon between $^{13}$C nuclei, so that most of the 31 residues were not observed (FIGS. 12 and 13). On the other hand, in Pro (3) illustrated in the present invention, the α-position and the γ-position were specifically labeled with $^{13}$C and $^1$H, and the relaxation influence has been eliminated as much as possible. As a result, it became possible to observe proton-derived signals of the α-position corresponding to 31 residues in the MSG incorporating Pro (3) (FIGS. 14 to 16).

What is claimed is:

1. A stable isotope-labeled amino acid for constituting a protein, satisfying all of the following conditions (1) to (3):
   (1) two or more carbon atoms are labeled with $^{13}$C;
   (2) the two or more carbon atoms labeled with $^{13}$C include a carbon atom of a methyl group, a carbon atom other than the carbon atom of the methyl group, or a combination thereof, wherein the carbon atom other than the carbon atom of the methyl group has one $^1$H directly bonded thereto, and the carbon atom of the methyl group has at least one $^1$H directly bonded thereto; and
   (3) carbon atoms adjacent to all the $^{13}$C are all $^{12}$C,
   wherein the amino acid is glutamic acid (Glu), isoleucine (Ile), lysine (Lys), leucine (Leu), methionine (Met), proline (Pro), glutamine (Gln), arginine (Arg), threonine (Thr), or valine (Val); and
   when the amino acid is leucine (Leu), a carbon atom of the methylene group present at the side chain of the amino acid is labeled with $^{13}$C, and one of two hydrogen atoms directly bonded to the $^{13}$C is stereo-selectively labeled with $^2$H.

2. The stable isotope-labeled amino acid according to claim 1, wherein (4) the number of carbon atoms located between the $^{13}$C having $^1$H directly bonded thereto and another carbon atom having $^1$H directly bonded thereto is three or less.

3. The stable isotope-labeled amino acid according to claim 2, wherein (5) the other carbon atom having $^1$H directly bonded thereto is labeled with $^{13}$C.

4. The stable isotope-labeled amino acid according to claim 1, wherein (6) a carbon atom of at least one methylene chain among methylene chains present at side chains of the amino acid is labeled with $^{13}$C, and one of two hydrogen atoms directly bonded to the $^{13}$C is stereo-selectively labeled with $^2$H.

5. The stable isotope-labeled amino acid according to claim 1, wherein (7) one of two hydrogen atoms directly bonded to a $^{12}$C carbon atom of a methylene chain present at the side chain of the amino acid is labeled with $^2$H, or both of the two hydrogen atoms are $^1$H or $^2$H.

6. The stable isotope-labeled amino acid according to claim 1, wherein (8) in a case where pro-chiral gem-methyl groups are present, one of the gem-methyl groups is labeled with $^{12}$C$^2$H$_3$ or $^{13}$C$^2$H$_3$.

7. A stable isotope-labeled amino acid, which is represented by one of the following ten structural formulas:

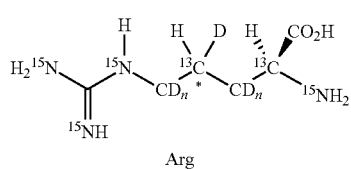

Arg

-continued

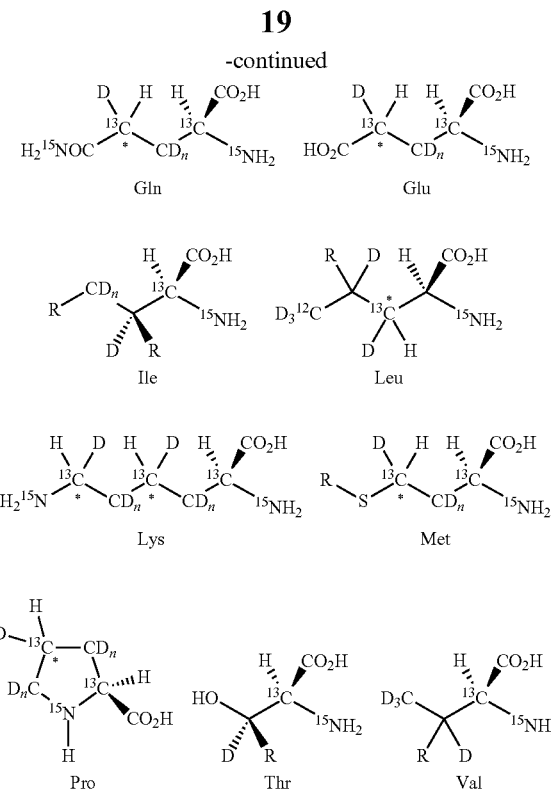

wherein R represents $^{13}C^1H_3$, $^{13}C^1H_2D$, or $^{13}C^1HD_2$, H has the same meaning as $^1H$, D has the same meaning as $^2H$, C has the same meaning as $^{12}C$, * represents a stereogenic center, the amino acids are any one of enantiomers with respect to the stereogenic center, n represents any one of 0 to 2, and in the case where n is 1, the amino acid may be a racemate or any one of enantiomers with respect to a carbon atom to which the corresponding deuterium is bonded.

8. A stable isotope-labeled amino acid, which is represented by one of the following ten structural formulas:

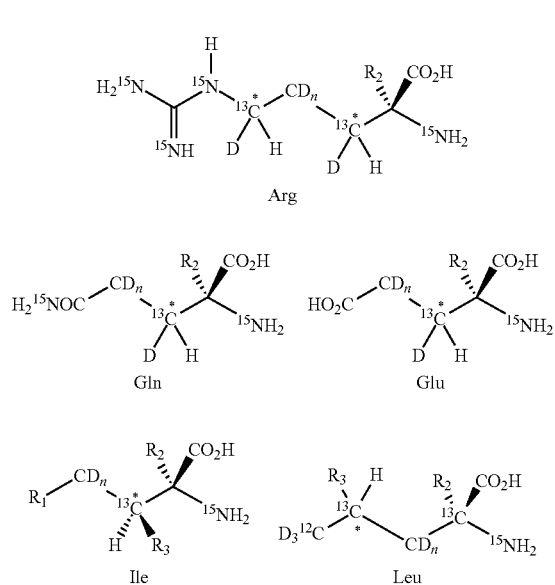

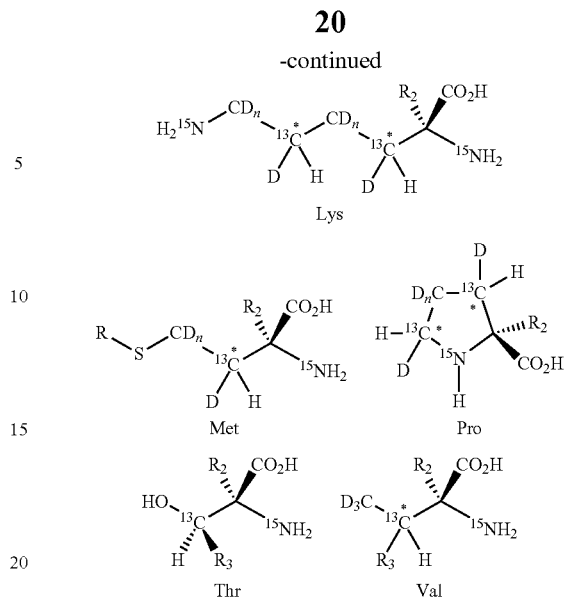

wherein R represents $^{13}C^1H_3$, $^{13}C^1H_2D$, or $^{13}C^1HD_2$, $R_2$ represents $^1H$ or $^2H$, $R_3$ represents $^{12}C^1H_3$, $^{12}C^1H_2D$, or $^{12}C^1HD_2$, H has the same meaning as $^1H$, D has the same meaning as $^2H$, C has the same meaning as $^{12}C$, * represents a stereogenic center, the amino acids are any one of enantiomers with respect to the stereogenic center, n represents any one of 0 to 2, and in the case where n is 1, the amino acid may be a racemate or any one of enantiomers with respect to a carbon atom to which the corresponding deuterium is bonded.

9. A composition comprising at least one of the stable isotope-labeled amino acids according to claim 1.

10. A composition comprising at least one of the stable isotope-labeled amino acids according to claim 7, which further comprises at least one of stable isotope-labeled amino acids represented by one of the following nine structural formulas:

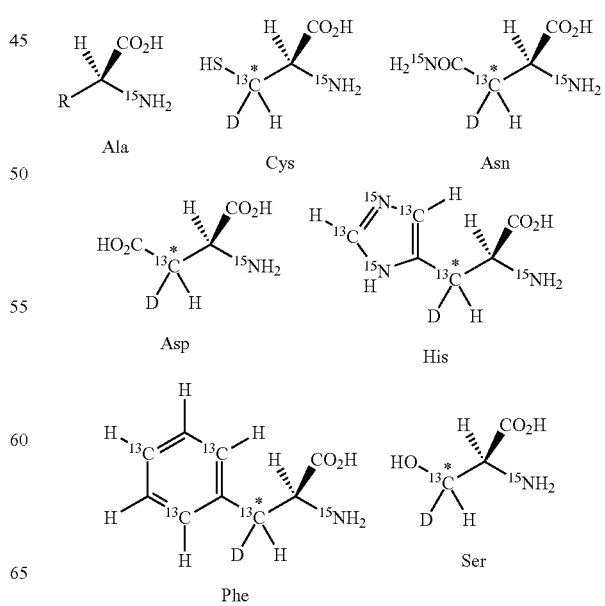

-continued

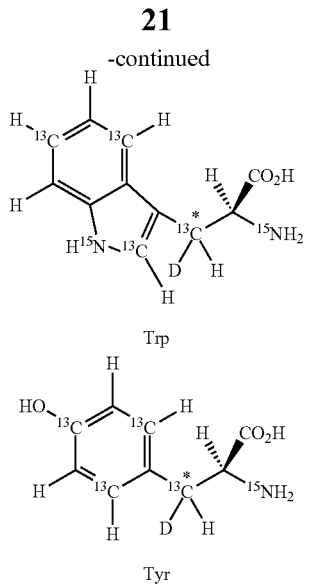

Trp

Tyr wherein R represents $^{13}C^1H_3$, $^{13}C^1H_2D$, or $^{13}C^1HD_2$, H has the same meaning as $^1H$, D has the same meaning as $^2H$, C has the same meaning as $^{12}C$, * represents a stereogenic center, and the amino acids are any one of enantiomers with respect to the stereogenic center.

11. A method for incorporating a stable isotope-labeled amino acid into a protein, comprising the step of synthesizing a protein using cultured cells, microorganisms, or a cell-free protein synthesis system in presence of the stable isotope-labeled amino acid according to claim 1.

12. An NMR structural analysis method for a protein, comprising the step of measuring an NMR spectrum of a solution of a purified protein obtained by the method for incorporating a stable isotope-labeled amino acid into a protein according to claim 11.

13. A composition comprising at least one of the stable isotope-labeled amino acids according to claim 8, which further comprises at least one of stable isotope-labeled amino acids represented by one of the following nine structural formulas:

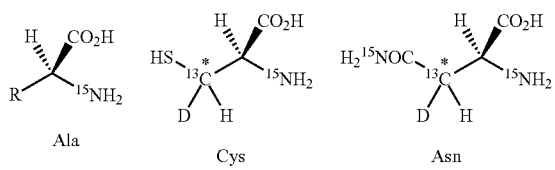

Ala       Cys       Asn

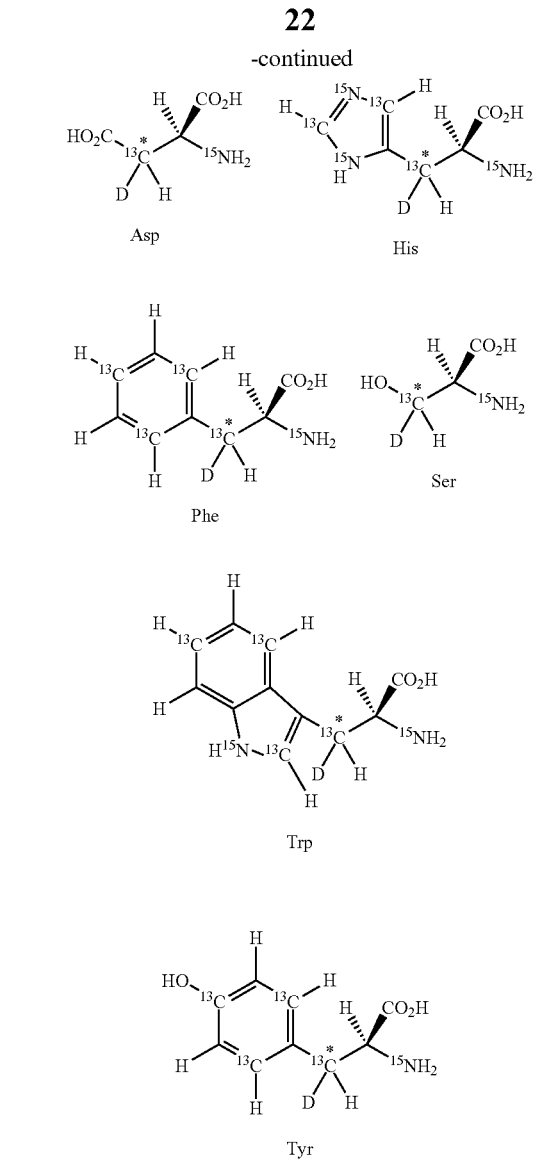

Asp       His

Phe       Ser

Trp

Tyr wherein R represents $^{13}C^1H_3$, $^{13}C^1H_2D$, or $^{13}C^1HD_2$, H has the same meaning as $^1H$, D has the same meaning as $^2H$, C has the same meaning as $^{12}C$, * represents a stereogenic center, and the amino acids are any one of enantiomers with respect to the stereogenic center.

* * * * *